US012408991B2

(12) United States Patent
Barak et al.

(10) Patent No.: US 12,408,991 B2
(45) Date of Patent: Sep. 9, 2025

(54) DYNAMIC DEFORMATION TRACKING FOR NAVIGATIONAL BRONCHOSCOPY

(71) Applicant: Magnisity Ltd., Hod-HaSharon (IL)

(72) Inventors: Ron Barak, Tel-Aviv (IL); Benjamin Greenburg, Hod-HaSharon (IL)

(73) Assignee: Magnisity Ltd., Hod-HaSharon (IL)

( * ) Notice: Subject to any disclaimer, the term of this patent is extended or adjusted under 35 U.S.C. 154(b) by 256 days.

(21) Appl. No.: 18/266,317

(22) PCT Filed: Dec. 9, 2021

(86) PCT No.: PCT/IL2021/051475
§ 371 (c)(1),
(2) Date: Jun. 9, 2023

(87) PCT Pub. No.: WO2022/123577
PCT Pub. Date: Jun. 16, 2022

(65) Prior Publication Data
US 2024/0041535 A1 Feb. 8, 2024

Related U.S. Application Data

(60) Provisional application No. 63/238,165, filed on Aug. 29, 2021, provisional application No. 63/123,590, filed on Dec. 10, 2020.

(51) Int. Cl.
G06T 19/00 (2011.01)
A61B 34/20 (2016.01)
(Continued)

(52) U.S. Cl.
CPC ............ *A61B 34/20* (2016.02); *G06T 19/003* (2013.01); *G06T 19/20* (2013.01); *A61B 1/2676* (2013.01);
(Continued)

(58) Field of Classification Search
None
See application file for complete search history.

(56) References Cited

U.S. PATENT DOCUMENTS 9,622,831 B2 4/2017 Azizian et al.
10,085,671 B2 10/2018 Duindam
(Continued)

FOREIGN PATENT DOCUMENTS

EP 2849669 11/2018
WO WO 2015/119935 8/2015
(Continued)

OTHER PUBLICATIONS

International Search Report and the Written Opinion Dated Apr. 3, 2022 From the International Searching Authority Re. Application No. PCT/IL2021/051475. (18 Pages).
(Continued)

*Primary Examiner* — Robert J Craddock

(57) ABSTRACT

Systems and methods for tracking movement of a catheter within airways of a lung. A deformable model of the lung represents airways of the lung as airway segments joined at bifurcations. Deformation of the lung model uses modification of the angles and/or positions of the airway segments with respect to each other. An initial model may be generated, for example, based on segmentation of a CT image. A baseline deformable registration of the initial model to a lung shape of the patient at the beginning of the procedure may be established from position measurements of the catheter along plurality of different pathways. Optionally, the baseline registration is dynamic according to respiratory phase. Relative to the baseline registration, real-time changes in lung shape may be modeled by using further
(Continued)

measurements obtained using the catheter as it navigates to a target, preferably using position sensors distributed along the catheter body.

45 Claims, 13 Drawing Sheets

(51) Int. Cl.
*G06T 19/20* (2011.01)
*A61B 1/267* (2006.01)

(52) U.S. Cl.
CPC .............. *A61B 2034/2051* (2016.02); *A61B 2034/2065* (2016.02); *G06T 2210/41* (2013.01); *G06T 2219/2021* (2013.01)

(56) References Cited

U.S. PATENT DOCUMENTS

| | | | |
|---|---|---|---|
| 10,314,656 | B2 | 6/2019 | Chopra |
| 10,499,993 | B2 | 12/2019 | Chopra et al. |
| 10,610,306 | B2 | 4/2020 | Chopra |
| 10,966,790 | B2 | 4/2021 | Chopra et al. |
| 11,202,680 | B2 | 12/2021 | Donhowe et al. |
| 11,376,075 | B2 | 7/2022 | Chopra et al. |
| 2013/0303893 | A1 | 11/2013 | Duindam et al. |
| 2016/0073928 | A1 | 3/2016 | Soper et al. |
| 2017/0189118 | A1 | 7/2017 | Chopra et al. |
| 2018/0078318 | A1 | 3/2018 | Barbagli et al. |
| 2018/0296281 | A1 | 10/2018 | Yeung et al. |
| 2018/0368917 | A1 | 12/2018 | Dekel et al. |
| 2019/0254752 | A1* | 8/2019 | Chopra .................. G06T 19/20 |
| 2019/0304091 | A1 | 10/2019 | Averbuch et al. |
| 2019/0320878 | A1 | 10/2019 | Duindam et al. |
| 2019/0350659 | A1 | 11/2019 | Wang et al. |
| 2019/0365486 | A1 | 12/2019 | Srinivasan et al. |
| 2020/0000526 | A1 | 1/2020 | Zhao |
| 2020/0179060 | A1 | 6/2020 | Kopel et al. |
| 2022/0071715 | A1 | 3/2022 | Donhowe et al. |

FOREIGN PATENT DOCUMENTS

| | | |
|---|---|---|
| WO | WO 2020/182997 | 9/2020 |
| WO | WO 2021/048837 | 3/2021 |
| WO | WO 2021/194803 | 9/2021 |
| WO | WO 2022/123577 | 6/2022 |
| WO | WO 2022/146952 | 7/2022 |
| WO | WO 2022/146992 | 7/2022 |
| WO | WO 2022/192392 | 9/2022 |
| WO | WO 2023/037367 | 3/2023 |

OTHER PUBLICATIONS

International Search Report and the Written Opinion Dated Dec. 8, 2022 From the International Searching Authority Re. Application No. PCT/IL2022/050978. (11 Pages).

Supplementary European Search Report and the European Search Opinion Dated Sep. 12, 2024 From the European Patent Office Re. Application No. 21902880.0. (12 Pages).

Supplementary European Search Report and the European Search Opinion Dated Jun. 5, 2025 From the European Patent Office Re. Application No. 22866883.6. (6 Pages).

* cited by examiner

DYNAMIC DEFORMATION TRACKING FOR NAVIGATIONAL BRONCHOSCOPY

RELATED APPLICATIONS

This application is a National Phase of PCT Patent Application No. PCT/IL2021/051475 having International filing date of Dec. 9, 2021, which claims the benefit of priority under 35 USC § 119 (e) of U.S. Provisional Patent Application Nos. 63/123,590 filed on Dec. 10, 2020, and 63/238,165 filed on Aug. 29, 2021. The contents of the above applications are all incorporated by reference as if fully set forth herein in their entirety.

FIELD AND BACKGROUND OF THE INVENTION

The present invention, in some embodiments thereof, relates to the field of bronchoscopy, and more particularly, but not exclusively, to electromagnetic navigational bronchoscopy.

Systems for navigating and/or monitoring probes moving within the lung have been proposed and/or marketed, including non-robotic navigation guided by single-sensor electromagnetic sensing with fluoroscopy); robotic navigation guided by fiber-optics shape sensing; and robotic navigation guided by single-sensor electromagnetic sensing. Other systems known in the art include fluoroscopy-based systems, CBT (cone-beam CT) guided systems, and video-registration based bronchoscopy.

SUMMARY OF THE INVENTION

According to an aspect of some embodiments of the present disclosure, there is provided a method of tracking positioning of an interventional instrument relative to airways of a lung, the method including: accessing a skeletonized model of airways of the lung, the model including a plurality of airway segments connected at bifurcations; accessing anatomically-defined constraints which limit changes to the shape of the skeletonized model; accessing measurements indicative of a plurality of positions along the interventional instrument and within the lung; and modifying within the model relative angles and positions of airway segments at one or more of the bifurcations, the modification being calculated by: reducing modeled error between a shape of the lung as indicated by the plurality of positions and an arrangement of the airway segments corresponding to the plurality of positions, and limiting, using the anatomically-based constraints, how shapes of the airways can change to reduce the modeled error.

According to some embodiments of the present disclosure, the modifying includes modifying relative angles of airway segments joined at a common bifurcation, wherein the common bifurcation is not traversed by the interventional instrument extending between the plurality of positions.

According to some embodiments of the present disclosure, the anatomically-based constraints comprise resistance of airways at a common bifurcation to increasing change of their relative angles.

According to some embodiments of the present disclosure, the anatomically-based constraints comprise anchoring forces exerted from a distal side of at least some of the airway segments.

According to some embodiments of the present disclosure, the anatomically-based constraints comprise limitations on bending along the length of at least some of the airway segments.

According to some embodiments of the present disclosure, the anatomically-based constraints comprise limitations on the separate movement of airway segments linked to each other through the parenchyma of the lung.

According to some embodiments of the present disclosure, the anatomically-based constraints comprise limitations on the airway segments forming a global shape which is inconsistent with a range of a global shapes represented by a data set including a plurality of global shapes.

According to some embodiments of the present disclosure, testing consistency of the airway segments shape with the range of global shapes includes applying a machine learning product configured to score the airway segments shape according to its likelihood of belonging within the range of global shapes.

According to some embodiments of the present disclosure, the range of global shapes is derived from measurements of a plurality of measured lungs.

According to some embodiments of the present disclosure, the range of global shapes is derived from modified versions of the skeletonized model, pre-calculated and accessed as part of the anatomically defined constraints.

According to some embodiments of the present disclosure, the anatomically-based constraints comprise limitations on airway segments representing lung portions along the plurality of positions forming a branch shape which is inconsistent with a range of a branch shapes represented by a data set including a plurality of branch shapes.

According to some embodiments of the present disclosure, testing consistency of the airway segments branch shape with the range of branch shapes includes applying a machine learning product configured to score the airway segments branch shape according to its likelihood of belonging within the range of branch shapes.

According to some embodiments of the present disclosure, the range of branch shapes is derived from measurements of a plurality of measured lungs.

According to some embodiments of the present disclosure, the range of global shapes is derived from modified versions of the skeletonized model, pre-calculated and accessed as part of the anatomically defined constraints.

According to some embodiments of the present disclosure, the method includes constructing the skeletonized model, based on segmentation of a CT image of the lung.

According to some embodiments of the present disclosure, the constructing includes skeletonizing the segmentation of the CT image, identifying bifurcations in the skeletonization, and assigning parameter values to the bifurcations representing relative angles of the bifurcations.

According to some embodiments of the present disclosure, the measurements accessed are measurements made along a plurality of different airway tracks using the interventional instrument in different positions of the interventional instrument at different times; the relative angles of airway segments are assigned to the bifurcations to conform to an imaged geometry of the lung; and the modifying modifies the relative angles of the airway segments according to changes in lung position between a time that the geometry of the lung was imaged, and a time of measuring along the plurality of different airway tracks.

According to some embodiments of the present disclosure, the accessed measurements are associated by their time of measurement with a phase of respiration; and the modifying modifies the relative angles to create a phase-varying skeletonized model of the airways of the lung that represents the shape of the lung during a plurality of different respiratory phases, based on the respiratory phase associations of the accessed measurements.

According to some embodiments of the present disclosure, the modifying is performed for new measurements associated with a phase of respiration; and modifies the phase-varying skeletonized model of the airways, according to both the positions of the new measurements and their associated phase of respiration.

According to some embodiments of the present disclosure, measurements are used in the modifying of relative angles of airway segments at different modeled respiratory phases according to a weighting depending on a difference between the respiratory phase associated with each measurement, and the different modeled respiratory phase.

According to some embodiments of the present disclosure, the shape of the lung during the plurality of different respiratory phases is represented by: a state of the lung at a first respiratory phase calculated by the modifying from the phase-associated measurements; a state of the lung at a second respiratory phase calculated by the modifying from the phase-associated measurements; and the lung at at least a third respiratory phase, calculated by interpolation of the lung shape between the first and second phases.

According to some embodiments of the present disclosure, the shape of the lung during the plurality of different phases is further represented by the lung at a fourth respiratory phase.

According to some embodiments of the present disclosure, the third and fourth respiratory phases are both equally spaced between the first and second respiratory phases, and different from each other.

According to some embodiments of the present disclosure, the phase of respiration is determined based on movements of markers attached to an exterior surface of a body including the lung and its airways.

According to some embodiments of the present disclosure, the method includes displaying an image representing the arrangement of the airway segments of the model.

According to some embodiments of the present disclosure, the method includes displaying an object in the image associated with the lung model, wherein a position of object is updated according to changes in the arrangement of the airway segments.

According to some embodiments of the present disclosure, the method includes associating the position of the object to a position of at least one of the airway segments, and moving the object in accordance with movements of the associated at least one of the airways segments.

According to some embodiments of the present disclosure, the image also represents a slice of a 3-D image of the lung in a known correspondence with the skeletonized model of the airways of the lung, the slice being selected to extend along a portion of the displayed lung corresponding to airways along which the interventional instrument extends.

According to some embodiments of the present disclosure, the known correspondence between the skeletonized model of the airways of the lung and the 3-D image of the lung is established by deriving the skeletonized model of the airways from a segmentation of the 3-D image of the lung.

According to some embodiments of the present disclosure, the displayed image includes a 3-D representation of the lung, and the slice of the 3-D image is curved out of a planar configuration to follow a 3-D configuration of the interventional instrument.

According to some embodiments of the present disclosure, the displayed image represents the interventional instrument flattened into a planar representation, with the slice of the 3-D image flattened along with it.

According to some embodiments of the present disclosure, the relative angles of airway segments are assigned to the bifurcations to conform to a geometry of the lung imaged during a first period, modified by changes to the geometry of the lung determined based on further measurements measured during a second period; and the measurements accessed are measurements made during a third period, along the interventional instrument, and while the interventional instrument remains in a same position; the modifying modifies the relative angles of the airway segments according to changes in lung position between the second and third periods.

According to some embodiments of the present disclosure, the method includes repeatedly: accessing successive sets of the measurements; and modifying the relative angles of the airway segments based on each successive set of measurements.

According to some embodiments of the present disclosure, the modifying includes: identifying new values for the relative angles which reduce the error between the shape of the lung as indicated by the plurality of positions and an arrangement of the airway segments corresponding to the plurality of positions; filtering the new values based on previous values of the relative angles, to reduce a magnitude of change from the previous values; and using the new values to produce the calculated modification.

According to some embodiments of the present disclosure, the filtering increases error between the shape of the lung as indicated by the plurality of positions and an arrangement of the airway segments corresponding to the plurality of positions, compared to the new values identified pre-filtering.

According to some embodiments of the present disclosure, the error is reduced incompletely by the modifying between each successive set of measurements.

According to some embodiments of the present disclosure, the modifying includes modifying the relative angles differently in a plurality of different copies of the skeletonized model; and including: repeating the accessing measurements and modifying for each of the different copies using new measurements; selecting one of the different copies based on a more plausible representation of the lung shape; continuing to repeat the accessing measurements and modifying using just the selected copy.

According to some embodiments of the present disclosure, the modifying includes perturbing the relative angles of airway segments in the modification to calculate a perturbed modification; identifying that the perturbed modification reduces the error more than the pre-perturbation modification; and using the perturbed modification to perform the modifying.

According to an aspect of some embodiments of the present disclosure, there is provided a computer memory storage medium storing a deformable model of a lung, the model including: data elements corresponding to: a skeletonized representation of a branched structure of airways of the lung, and for each of a plurality of bifurcations of the branched structure, a representation of the orientations of the branches of the branched structure; and computer instructions configured to instruct a processor to modify the model to satisfy provided geometric constraints by modifying the representations of relative orientations of the branches of the branched structure.

According to some embodiments of the present disclosure, the plurality of bifurcations includes bifurcations up to a third level of branching of the branched structure.

According to some embodiments of the present disclosure, the computer instructions instruct the processor to modify the representations of the orientations of the branches of the branched structure without modifying distances along segments of the branched structure.

According to some embodiments of the present disclosure, the computer instructions instruct the processor to propagate changes modifying relative orientations of branches in a parent bifurcation to changes modifying spatial offsets and orientations of branches of child bifurcations of the parent bifurcation.

According to an aspect of some embodiments of the present disclosure, there is provided a system for tracking movement of an interventional instrument within airways of a lung, the system including a processor and memory holding instructions which instruct the processor to: access a 3-D representation of a current shape and positioning of the interventional instrument; access a model of the airways representing airway segments, including bifurcations of airway segments; and match the airway segments to the current shape and positioning of the interventional instrument; wherein the processor is instructed to: determine rotational modifications of branches of the bifurcations, based on improvement to correspondence of the airway segments to the current shape and positioning of the interventional instrument, and apply the modifications to the model.

According to some embodiments of the present disclosure, the rotational modifications are applied to modeled airway segments corresponding to sections of the airways along which the interventional instrument extends.

According to some embodiments of the present disclosure, the processor is instructed to access measurements of body motion; and wherein the processor is instructed to modify orientations of the airway segments to modify the model of the airways to match a change in lung shape corresponding to the measurements of body motion.

According to some embodiments of the present disclosure, the modifications are applied to the model using position data associated to the bifurcations as control points.

According to some embodiments of the present disclosure, rotational modifications of different types are separately weighted in their availability to improve matching of the airway model to a change in lung shape corresponding to the measurements of body motion.

According to some embodiments of the present disclosure, rotational modifications of different types are separately weighted in their availability to improve correspondence of the airway segments to the current shape and positioning of the interventional instrument.

According to some embodiments of the present disclosure, longitudinal bending rotational modifications are weighted as more available to improve correspondence than longitudinal twisting rotational modifications.

According to an aspect of some embodiments of the present disclosure, there is provided a method of registering interventional instrument position data to an imaged lung shape, the method including: receiving a baseline lung airways model constructed based on the imaged lung shape of a lung; measuring, at a later time, and using one or more intra-lung probes, positions along a plurality of branches of airways of the lung, including at least two different branches of a same bifurcation of the airways; modifying the baseline lung airways model to register with the measured positions and produce a deformed baseline lung airways model, wherein the deformed baseline lung airways model represents the lung airways in a plurality of respiratory phases; determining, based on measurements indicative of a current shape of the lung, a transformation applicable to the deformed baseline lung airways model to adjust it to indicate a current shape of the lung; and displaying an image showing the deformed baseline lung airways model, transformed according to the transformation.

According to some embodiments of the present disclosure, the measurements of positions along the plurality of branches of airways of the lung are each associated with a respiratory phase, and the representations of the lung airways in different phases of the plurality of respiratory phases are generated using the associations of the measurements with different respiratory phases.

According to some embodiments of the present disclosure, the determining a transformation includes: using a respiratory phase corresponding to the indicated current shape of the lung to determine a respiratory phase-dependent shape of the deformed baseline lung airways model; and calculating the transformation to transform the determined respiratory phase-dependent shape to the indicated current shape of the lung.

According to some embodiments of the present disclosure, in the deformed baseline lung airways model, the shape of the lung during the plurality of respiratory phases is represented by: a state of the lung at a first respiratory phase, produced by the modifying of the baseline lung airways model; a state of the lung at a second respiratory phase, produced by the modifying of the baseline lung airways model.

According to some embodiments of the present disclosure, the determining includes generating from the deformed baseline airways model a baseline shape of the lung in a third respiratory phase, calculated by interpolation of the lung shape between the first and second phases.

According to some embodiments of the present disclosure, the shape of the lung during the plurality of respiratory phases further includes a state of the lung at a fourth respiratory phase, produced by the modifying of the baseline lung airways model.

According to some embodiments of the present disclosure, the third and fourth respiratory phases are each of: similarly spaced in phase between the first and second respiratory phases, and different from each other.

According to an aspect of some embodiments of the present disclosure, there is provided a method of displaying features along a convoluted pathway through an anatomical structure, including: accessing a 3-D image of the anatomical structure; defining a pathway through the anatomical structure; calculating: spatial correspondence of positions along the pathway with locations within the 3-D image, and a surface extending through the 3-D image which includes the locations within the 3-D image; and displaying a 3-D display image which shows the pathway extending through 3-D space, together with data from positions of the 3-D image of the anatomical structure defined by the surface; wherein: the pathway is defined repeatedly using measurements of at least one dynamically changing parameter of a shape of the anatomical structure, and the calculating and displaying are repeated for each repeated defining of the pathway.

According to some embodiments of the present disclosure, the surface is calculated as a strip extending along the pathway on either side of the pathway.

According to some embodiments of the present disclosure, the strip extends to about an equal distance on either side of the pathway.

According to some embodiments of the present disclosure, the method includes accessing a 3-D model of a portion of the anatomical structure in a known spatial correspondence with the pathway, and including display of the 3-D model of the anatomical structure in the 3-D display image.

According to some embodiments of the present disclosure, the 3-D model of the portion of the anatomical structure also dynamically changes.

According to some embodiments of the present disclosure, the anatomical structure includes airways of a lung.

According to some embodiments of the present disclosure, the pathway extends through airways of a lung.

According to some embodiments of the present disclosure, the measurements of at least one dynamically changing parameter comprise position measurements of an interventional instrument positioned along the pathway.

According to some embodiments of the present disclosure, the position measurements of the interventional instrument positioned along the pathway include position measurements from a plurality of locations along the pathway.

According to some embodiments of the present disclosure, the measurements of the at least one dynamically changing parameter are associated by their time of measurement with a phase of respiration.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable medium to receive instructions and/or data therefrom, process them, and/or store processing results in the same or another computer readable medium. The processing performed (optionally on the data) is specified by the instructions, with the effect that the processor operates according to the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings.

DESCRIPTION OF SPECIFIC EMBODIMENTS OF THE INVENTION

Figure 1:
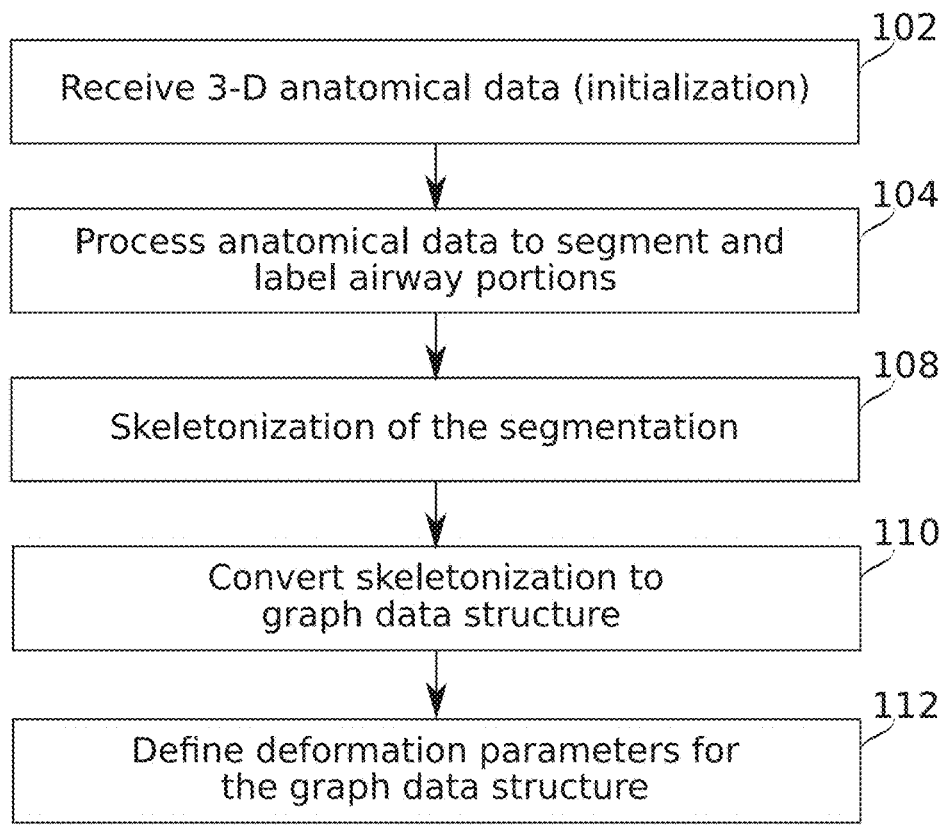
FIG. 1 is a schematic flowchart representing a method of generating a deformation model of a lung, according to some embodiments of the present disclosure.

The present invention, in some embodiments thereof, relates to the field of bronchoscopy, and more particularly, but not exclusively, to electromagnetic navigational bronchoscopy.

Overview

A broad aspect of some embodiments of the present disclosure relates to robotic navigation of a probe within the branched and dynamically moving airways of a living lung.
Interventional Instrument Tracking In The Lung The lung's complex structure poses a problem for the field of navigational guidance for bronchoscopy procedures. Compounding this, the lungs are flexible and in dynamic motion, so that a positioning system which does not account for lung movements is subject to inherent error.

Use of fluoroscopy, CBCT or EBUS (endobronchial ultrasound) to track probe and/or target positioning potentially increases navigation accuracy, with the tradeoffs of, e.g., additional equipment, increased procedure complexity, and/or potential radiation dose to the patient and/or physician.

Another approach uses an ENB (electromagnetic navigational bronchoscopy) system to determine probe localization. Such a system generates electromagnetic fields using a dedicated antenna (or transmitter), and senses them using an EM (electromagnetic) sensor. The EM sensor may provide 6-DOF (degrees of freedom) position and orientation information of the tip relative to the localization (transmitter) coordinates. This EM localization technology has potential advantages for medical use: for example, the body is substantially transparent to the generated EM fields, and no ionizing radiation is used.

Traditional ENB systems use a tip-positioned EM sensor. Limited to such a sensor, it is difficult to perform position tracking which adequately distinguishes, e.g., between controlled motion (relative to the airways of the lung), and motion induced by movement of the lung itself. One method proposed to overcome this limitation is the use of fiber optics for achieving catheter (or other interventional instrument) shape sensing. Shape sensing may allow the interventional instrument to sense relative positioning among its own parts. A tip-positioned EM sensor, for example, may be used to provide an anchor position relative to the lung being navigated.

Herein, the term "interventional instrument" is used as an umbrella term which stands in more generally for flexible instruments comprising a thin and longitudinally extended body, which are used by advancing them distally through a body lumen to reach a distal target. Generally, the advance is performed using distal-ward pressure from a proximal side of the instrument, so there is some stiffness to the instrument, even though it is flexible. Examples of interventional instruments include catheters, bronchoscopes, and endoscopes. Herein, where an instrument is described as "similar" to a catheter, bronchoscope, or endoscope, these characteristics are being referenced.

In some embodiments of the present disclosure, EM sensing capabilities are extended to allow tracking to extend proximally along the catheter body from its tip. For brevity, this is also referred to herein as "full interventional instrument" tracking. It should be understood that "full interventional instrument" refers not necessarily to the entirety of the instrument's length, but rather to a length sufficiently long (e.g, at least 5 cm, at least 10 cm, at least 20 cm) as to help overcome positioning errors and/or ambiguities which tip-only sensing may be prone to. This may be, for example, the entire length inserted to the airways being navigated, or the entire length up to a reference point such as a reference point established along the trachea.
Approaches to Instrument-to-Anatomy Coordinate Registration The lungs comprise a complex tree-like hierarchy system of airways. The complexity creates potential difficulties for video guidance; particularly in the periphery of the lungs, where airways become smaller and may seem identical, and where the number of bifurcations increases exponentially. Also, image quality may be degraded, for example, by mucus present in the lungs, making it difficult to navigate based on video alone. Methods, as known in the art, of achieving surgically useful registration between probe position and the anatomy it is traversing may be performed in multiple stages using multiple sources of information.

Rough registration: In some NB (navigational bronchoscopy) systems, registration between a system of 3-D localization coordinates (LOC) and the patient's preoperative CT or MRI is performed, and this registration may help manage these difficulties. Herein a "localization system" refers to a system of coordinates within which a probe's position is initially described (or "localized"). That position is referred to herein as being described by the probe's "localization coordinates".

The CT or MRI image contains 3-D information about the lungs, and in particular accurate positions and shapes of the patient's airway. The airways are resolved above a certain diameter which itself depends on the resolution of the CT or MRI scan. The CT or MRI imager, in effect, maps the airways, which are the "roads" along which an interventional instrument may travel. The map is provided to the NB system, which uses it to provide navigational instructions to the physician: for example, which turns to take, what distance to drive etc. Navigational instructions may be presented as overlaid on top of a static preoperative CT scan (the "map") of the patient, and may be presented together with a pathway displaying the route to the target.

To display a localized interventional instrument at its true anatomical position inside the lungs, a correspondingly accurate registration (3D transformation) is applied to map measured 3-D interventional instrument localization coordinates to the CT-derived model of the patient's anatomy. One approach to constrain and/or calibrate the parameters of this transformation comprises attaching reference sensors to the patient at fixed anatomical positions, and using these to achieve rough registration between the anatomy and the localization system. The reference sensors move together with the patient so the system is aware of how the body lies in the localization coordinates. In some systems it may not be known how the reference sensors are actually positioned relative to the anatomy, and the reference sensors are used for the calculation of a LOC-to-anatomy registration relative to some separately determined baseline registration.

Refining rough registration: To generate a registration useful to distinguish between adjacent airways, the rough registration may be enhanced by additional information. For example, registration may be refined using the markings of several anatomical fiducials using the interventional instrument's tip inside the airways.

In one approach to this: in an initial video-assisted survey, a physician visually identifies major predefined airway bifurcations and marks them with the localized interventional instrument's tip. The marked positions are then gathered in LOC coordinates and matched with their anatomical (e.g., CT or MRI image) coordinates counterparts. From this, a LOC-to-anatomy registration is computed. This can be highly accurate at the proximity of the participating fiducials.

In another approach: a physician may perform an unsupervised survey with the interventional instrument inside the major airways of the lungs. By this survey, the physician collects positions of the interventional instrument in LOC coordinates. The unsupervised registration algorithm matches these with the "roads" known from the airways map, for example, using energy minimization optimization methods.

When enough samples are collected, a unique solution is found and initial LOC-to-anatomy registration is achieved. This may provide high accuracy, particularly at the area (typically the central area) of the lungs where the survey was performed. The LOC coordinates may be fixed relative to the patient bed (for example, where an antenna is installed) or may move with the patient by using standard reference sensor compensation methods.

Dynamic registration: It may be understood that while these approaches provide an initial registration between the LOC coordinates and the airways map, they do not address real-time registration inaccuracies due to the flexible and dynamic nature of the lungs.

The lungs change their shape as a result, for example, of: breathing, changes in body posture, and/or forces applied to the lungs by an interventional instrument moving within them, e.g., bronchoscope or other endoscope, catheter, tools used therewith, and/or similar surgical instruments. These (potentially among other causes), result in deviation between the initial registration and the real-time state of the airways anatomy relative to the localization system.

In some systems, registration is updated based on history. For example, instead of using just a single 6-DOF measurement of the interventional instrument's tip from the present time-frame, the interventional instrument's path is constructed over a short time window (e.g., a few seconds). The path is then searched inside the map to match some possible "roadway". As a result, instead of just localizing the interventional instrument's tip inside the airway, a longer path, traversed over time by the interventional instrument, is matched to the map. If interventional instrument takes, for example, a "right turn" at a certain bifurcation (e.g., as seen in the interventional instrument's path constructed from its history of samples), it is known that the final interventional instrument's position cannot lie on the left airway, it must be on the right side.

An aspect of some embodiments of the present disclosure relates to a parametric lung deformation model adjusted through the modification of parameters affecting associated airway segments of the lung model, while constraining modification of those parameters so that the airway segments move within anatomically-based constraints.

The inventors have found that by assigning parameters (e.g., up to about 50, 100, or 150; and far fewer than the number of voxels in the CT representation, and optionally even far fewer than the total number of bifurcations in the airways skeleton), the model is general enough to describe deformations the lungs may undergo due to, e.g., breathing, change of patient's posture, and/or forces applied by the bronchoscope or other endoscope, catheter, tools used therewith, and/or similar interventional instruments. The position and orientation of the interventional instrument along its body (i.e., position and orientation at a plurality of points along the interventional instrument body while it is inserted to a lung) is useful as source of data for updating those parameters as the lungs move, and move the interventional instrument body along with—or vice versa. In some embodiments, the interventional instrument body is tracked from its tip to at least the trachea.

In some embodiments, the model itself comprises a skeletonized representation of the airways of the lung. The skeletonized representation may be generated, for example, by performing a skeletonization operation on an airways segmentation performed on a CT or MRI image of a lung. Deformability is introduced into the lung model by parameterizing the bifurcations of the skeletonized representation; e.g., parameterizing the relative translations and orientations of segments joined at each bifurcation. Adjustments to the parameters of bifurcations in the larger (more proximal) airways are optionally allowed to propagate to more distal bifurcations, simulating relative movements of lobes of the lungs with respect to each other.

In some embodiments, constraints on the freedom to adjust bifurcation parameters are added to simulate the mechanical properties which limit the range of rearrangements which can occur at an individual bifurcation. Constraints provided, in some embodiments of the present disclosure include, for example, one or more of the following:

Restrictions on how much segments at a bifurcation can change their orientation (angle) relative to each other. This may include allowing relatively free movement for small angle changes, with increasing resistance to change with increasingly large changes in relative angle. In some embodiments, the resistance to angle change is also specified as function of airway diameter, airway wall thickness, and/or branch order, to reflect different relative stiffness at different bifurcations. Effects of such constraints on the model may include, for example, forcing a portion of segment rearrangement into bending along the segment length, rather than at the bifurcation itself. Where a plurality of bifurcations are involved, the model may "prefer" (due to the constraints) to bend more at some bifurcations, and less at others.

Anchoring exerted from a distal side of airway segments—that is, a side away from the branching structure of the airways which anchors them to the trachea. Some areas of the lung may be partially held in place through attachment to, inter-digitation with, and/or confinement by structures which are not part of the airway branch hierarchy; e.g., the pleura and septa. An effect of this constraint on the model may be, for example, to cause airway segments to skew their orientation relative to their proximally-anchoring bifurcation, so that they continue to point more-or-less toward their original distal-side position.

Airway segments modeled as mechanically interconnected laterally (that is, not through the branching structure itself), through the parenchyma of the lung. This linkage may be transmitted, e.g., through some airways separated from one another in the branching structure by more than one bifurcation proximally. An effect of this constraint on the model may be, for example to reduce the tendency of airway angles at two or more separate bifurcations to change their angles in directions which would pull segments apart too much, or push them together too much.

Airway segments modeled with flexibility along their length. An effect of this constraint is to relieve strains due to changes in segment angles bifurcations. This may also help with error reduction, since a bend in the interventional instrument along an airway segment can be accommodated by a corresponding parameter of the airway segment in the model.

It should be noted that the representation of anatomical constraints allows the model to propagate deformations beyond positions that were directly measured. Changes in measured shape may be most plausible (in terms of the model's configuration) in the context of more global changes in lung shape, extending to segments and/or bifurcations away from the current position of the interventional instrument that propagate to effects which interact with the constraints.

Another method of applying anatomically-based constraints to a model is to use the results of a machine learning algorithm which learns from provided inputs representing anatomically realistic configurations of lung airways. The provided inputs may be based on images of actual lungs, suitably skeletonized. Arrangements of the model's airway skeleton are judged according to whether they suitably match the arrangements on which the machine learning algorithm was trained.

In some embodiments, machine learning is hybridized with parameter-based (e.g., error-reduction based) judgements of the anatomical plausibility of an airways skeleton. For a training set, a plurality of skeletonized models of lungs are subjected to perturbations (e.g., shapes imposed and/or sensed by a model of the interventional instrument). A high-fidelity error-reduction model (with many constraints defined, e.g., most or all the types just listed) is applied to the perturbed model. The result may be computationally intensive to arrive at, but the error-reduction can occur off-line so that the computational time is less important. Machine learning is then applied to the training set just generated, e.g., by a training method known in the art. The result of the machine learning is then optionally used as a method of performing real-time judgements of lung airways shapes, potentially encapsulating results of the more computationally intensive method in a computationally less intensive form. The machine learning may be performed at the level of the whole lung skeleton (e.g., as modeled up to 3, 4, 5 or more branching orders), and/or on selected portion of the lung skeleton, for example, single branches occupied by the interventional instrument, preferably together with the next bifurcation which the modeled interventional instrument would encounter and traverse.

This type of representation provides potential advantages for realistic modeling of dynamically changing lung geometries, and/or for reducing the number of computations involved in updating a model lung geometry to match measurements of the modeled lung itself. In some embodiments, the updating occurs in real time, allowing the model to be used in dynamic tracking of the lung shape, e.g., during a navigational bronchoscopy procedure.

In identifying dynamic parameters of the lung model with bifurcation positions and angles, the model also creates potential synergy with lung geometry measurement methods that themselves readily provide bifurcation angle information. In particular, an interventional instrument traverses bifurcations as it is advanced into the lung. Changes in direction of the interventional instrument at distances corresponding to the modeled positions of bifurcations provide information about bifurcation positions and angles.

If only the tip of the interventional instrument is used for measurements, measured tip position and/or orientation information potentially becomes outdated as an indication of lung shape as the interventional instrument continues its distal advance. If a later lung deformation causes angle rearrangements at a bifurcation proximal to the current interventional instrument tip position, it is potentially ambiguous which bifurcation or bifurcations should be adjusted to bring the lung model back into an alignment that is consistent with the newly shifted interventional instrument tip position.

In some embodiments of the present invention, this ambiguity is addressed by simultaneously gathering position data from along a longitudinally extended region of the interventional instrument. Optionally the longitudinally extended region extends from the interventional instrument tip proximally back at least to the first lung bifurcation traversed by the interventional instrument. In this situation, the problem of dynamically identifying which bifurcations deform and by how much is constrained by data gathered in real time from portions of the interventional instrument occupying the locations of those bifurcations.

An aspect of some embodiments of the present disclosure relates to a two-stage process of registering a deformable model of a static lung shape to a dynamically changing lung shape, according to some embodiments of the present disclosure.

In some embodiments: in an initial deformable registration step, an unsupervised survey is performed (preferably using a fully tracked interventional instrument) to collect samples in LOC (localization coordinates of the spatially tracked interventional instrument). A deformable airways map is then fitted to the samples using energy minimization optimization method. This is an example of a method that provides an initial deformable registration between LOC and anatomy.

Optionally, in the presence of a reference sensor(s), a momentary breathing phase is assigned to each collected sample during registration. This allows for the deformable registration algorithm to fit two or more models, for example, one for "inhale" and one for "exhale", to the collected samples. The resulting 4-D position samples (3-D position+breathing phase), are collected in a breathing-interpolated airways map. Optionally another dimensionality is used, for example 7-D: three position degrees of freedom, three orientation degrees of freedom, and breathing.

After initial registration, a dynamic deformation tracking algorithm adjusts the deformation model in real-time to the deformable lungs to provide a realistic deformation tracking. The airways map from the preoperative CT or MRI is deformed accordingly, and placed into localization coordinates, to represent the true state of the airways during the procedure.

The model is fitted to the lungs by means of energy minimization optimization methods. The energy function incorporates both shape constraints (which restrict the solved deformation to just reasonable configurations, where reasonable is determined by a collection of constraints based on theoretically and/or observationally based limits on how the lung can move) and a target goal (which requires one or more localized interventional instruments to be inside the deformed airways).

The deformation algorithm performs fitting using inputs from any combination of localization system sources used as its target goal: e.g., one or multiple fully tracked or single sensor interventional instruments, with or without history data. There is a particular potential advantage, however, to providing to the deformation tracking algorithm real-time, fully tracked positions and orientations of one or multiple interventional instruments. The historical position of the interventional instrument tip in some location of the anatomy may become outdated if that location in the anatomy itself moves. However, the full shape of the interventional instrument "updates" with the anatomy, providing information particularly useful as a constraint on lung dynamics.

Using the deformation model for both initial registration as well as dynamic deformation tracking, the airways can then be displayed during NB procedure in their realistic state. The modeled lung "breathe" in sync with the patient in real-time, and otherwise deform dynamically as additional forces are applied. This allows the interventional instrument to be displayed in its true deformable-anatomical position inside the airways, potentially increasing overall system accuracy.

It may be noted that modeling deformations occurring at lung bifurcations other than (and particularly relatively far from) those currently being traversed by a measurement interventional instrument may be less fully constrained (due to a lack of direct, live measurement data). However—insofar as the lung model is being used to guide navigation toward a target at the end of the current track of the interventional instrument, the impact of this ambiguity is potentially reduced to irrelevancy. For example:

Some movements of lung regions away from the navigation track may be irrelevant, for having no effect on the target position.

Other such movements may have an effect on the target position via deformation forces exerted on bifurcations which are on (or close to) the current track of the interventional instrument. In this case, new measurements will detect the change, and allow at least the target-containing portion of the lung to be repositioned as necessary by appropriate deformation of the model.

A third possibility is for such off-track lung deformations to affect the geometry of yet-to-be-traversed portions of the lung airways on the way to the target. But these changes will generally be revealed as the interventional instrument continues its advance, allowing successive detection of geometrical changes in the more distal airway bifurcations, enabling successful navigation to the target. It may be understood that this applies to distal deformations more generally.

In principle, a portion of cases belonging to the third possibility might still introduce ambiguity in navigation by deforming a distal bifurcation so much that when the interventional instrument reaches it, one branch has "replaced" the other—that is, one branch occupies a position which is consistent with the model's current representation of the other branch. It is anticipated, however, that mechanical constraints on local tissue deformation will tend to spread such severe deformations over a relatively large longitudinal extent of the airways track, so that the incremental deformation experienced between two adjacent bifurcations may be assumed small enough that confusion between two bifurcation branches is avoided.

It may be noted, in any case, that even if one bifurcation branch deforms enough to be confused with (and replace) the positioning of other, it remains unlikely that the reverse will also be true. That case would be roughly equivalent to a 180° twist along a single segment joining two bifurcations, which is biomechanically implausible. Accordingly, where there is a perceived risk of ambiguity, both branches may be traversed in alternation, allowing the risk to be avoided.

An aspect of some embodiments of the present disclosure relates to the dynamic display of 3-D image data surfaces transformed to correspond to current positions of anatomical features they represent, based on real-time updating measurements indicative of shape of the represented anatomical features.

In some embodiments, a 3-D image is obtained at a time before an interventional procedure, which includes images of anatomical regions along a pathway which is to be traversed to reach an interventional target, and optionally the target itself. Particularly if it is a pathway defined according to lumens of a branched anatomical structure such as a lung, the pathway may be convoluted in shape—bending through 3-D space so as to be unconfined to any single plane in space.

The pathway may also be dynamic in shape; insofar as it changes between a time of imaging and a time of the interventional procedure itself, and/or changes even during the procedure. In the case of lungs, for example, the lungs may shift in position over time for any of the reasons recited above. In particular, during a procedure, the breathing cycle leads to constant changes in organ shape, and an interventional instrument may exert changing forces that induce movement and/or deformations of the organ.

The earlier-obtained 3-D image data may include features of contextual relevance to the ongoing procedure, such as: target size, shape, and/or position; and relative locations of potentially vulnerable structures such as blood vessels. It is a potential advantage for a physician to have displayed to them any of these or other structures, relative to the path along which an interventional instrument is travelling and/or is planned to travel, in its current and dynamically updated shape.

In some embodiments of the present disclosure, a method of displaying features along the convoluted pathway comprises calculating a surface along a given pathway which defines positions of data elements of the 3-D image. Data from along the surface is transformed in position so that it is registered to a current (and dynamically changing) shape of the pathway. The current shape of the pathway is determined by measurements indicative of it shape, e.g., a shape of an interventional instrument occupying the pathway or a portion thereof, a measurement indicative of a current lung inflation state, or another measurement.

The surface may be displayed (in its transformed, three dimensional shape) out to the limits of the extent of available image data, or it may be confined to a strip of data locations flanking the pathway. In addition to the surface, the pathway itself may be indicated. There may be another indication displayed together with the surface, such as a 3-D mesh indicative of a lumenal shape along which the pathway extends (e.g., an airways shape, or a shape of another lumenal anatomical structure such as blood vessels, digestive tract, urinary tract, or another anatomical structure).

In some embodiments, the pathway is transformed to a planar and/or linear path, and image data to either side of the pathway on the defined surface shown, together with the path, in a flattened image display. The image data are optionally taken from locations along a series of lines defined normal to the pathway at several locations. There is, however, no particular limitation that the surface must be flat along a direction normal to the pathway; it may be curved in this direction as well. In some embodiments, the surface is defined as a result estimated to optimally and jointly satisfy constraints of the pathway shape, as well as constraints such as to include portions of significant structures such as a target of an interventional procedure, and/or potential hazards along the pathway such as blood vessels.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Deformation Model

Reference is now made to FIG. 1, which is a schematic flowchart representing a method of generating a deformation model of a lung, according to some embodiments of the present disclosure.

In overview, lung imaging data is converted to a base model (preferably a skeletonized representation of lung airways). To this model, parameters are applied which describe how the base model may be deformed to match a particular condition of an actual lung.

In some embodiments, the deformation model (e.g., as next described) is defined to use a relatively small number of parameters to define results of the possible different deformation mechanisms discussed above. Potential advantages for defining a deformation model with a low number of parameters include avoiding over-fitting of the observed data by the model and speeding up the optimization process.

Lung deformation may be treated as a distributed property, insofar as one airway cannot be deformed much differently than its neighbors. Global parameters may be defined to describe deformation features such as: how the lungs globally expand or shrink during breathing, how one lung is deformed compared to the other due to forces applied by the bronchoscope, and/or how both lungs undergo some global stretch or shear (e.g., due to the patient's different postures). These deformation features are also significant to the overall accuracy of a navigating system. Being global in nature, these features can be described by just a few parameters and constraints.

The following model is used as a basis for the implementation of deformation modeling, in some embodiments of the present disclosure. The inventors have derived it from experimental results with rigid and semi-rigid lung phantoms, animal models and recorded human data. It should be understood that different models can be used by the deformation tracking algorithm, not limited to the particular parameterization below. The deformation tracking algorithm is generally indifferent to the specific parameterization of the model in use; but a good choice of model can reduce the risk of over-fitting and significantly boost the performance of the tracking algorithm.

The model, in some embodiments, is based on airways skeletonization, which provides centerlines of the airways in the lungs. The airways skeletonization is generated, for example after preparation of data as follows:

At block 102, in some embodiments, a patient's preoperative or early-operative CT, MRI, or other 3-D image is loaded into the system in an initialization stage prior to the NB procedure.

At block 104, in some embodiments, the CT or MRI image is processed. 3-D voxels belonging to the airways are segmented and marked (e.g., labeled in computer memory), using a segmentation method such as adaptive region growing, deep-learning 2-D/3-D CNNs (convolutional neural networks), a combination of both or any other suitable method. Optionally other anatomical features are segmented as well, for example, blood vessels, which, although not navigated in the NB procedure, may provide information about the shape of the lung and/or its freedom to change shape in different ways. For example, a blood vessel may constrain a lung lobe from bending or twisting in a certain direction, or beyond a certain amount. It should be understood that reference is here made to a CT or MRI image, which is an example of, more generally, any detailed source of anatomical information about a particular lung. While CT or MRI images may be considered present gold standards for providing such information, it is not excluded that present and/or future developments in the field of lung imaging may allow another source of anatomical information to be used, for example, information imaged based on future advances in X-ray imaging, magnetic resonance imaging, or another data gathering method.

In some embodiments, the airways segmentation produced by the operations of block 104 represents a binary 3-D volume in which each voxel is either 1 if it belongs to an airway or 0 otherwise. This provides an initial representation of airways map information used by the NB guidance system, as discussed above.

At block 108, in some embodiments, skeletonization is performed, as a step toward determining, from the 3-D binary volume of the segmentation produced in block 104, the tree structure of the airways.

Skeletonization transforms the raw airways segmentation volume into a tree-like structure which encodes the airways map. As a result of skeletonization, a 3-D segmented volume of tubes is converted to a graph of centerlines with radii.

At block 110, in some embodiments, the skeletonization produced at block 108 is further transformed into a graph data structure comprising nodes connected by edges. Each node represents a single tube of the segmentation (a centerline segment whether straight or curved of a certain length with constant or variable radius along it). Each edge (directed or undirected) which links a node pair represents connectivity of those tubes, between a proximal side of one tube and a distal side of another. Accordingly, the graph of block 110 represents the lungs as a tree (acyclic) graph of tubes.

The root of the tree graph is defined to be the trachea. The first bifurcation is the carina, and the rest of the airways hierarchy follows as descendants in the tree. The skeleton may be assessed for completeness by considering it as a compressed data representation of the airways segmentation, from which the segmented volume can be recovered, and performing reverse skeletonization-to-segmentation transform. A good match (as is found to be the case) with the original segmentation means that the skeleton encodes most of the information of the segmented volume. Since the skeleton is much smaller in size, and much easier to traverse and analyze, it provides potential advantages for use as a representation for the airways map.

Figure 2:
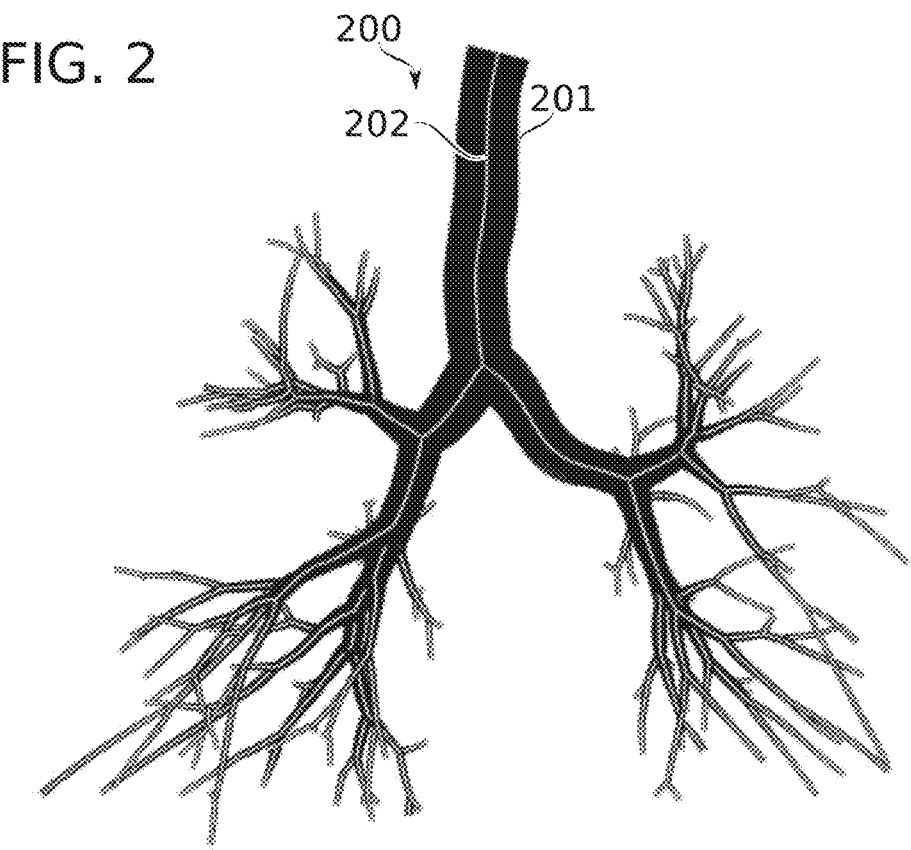
FIG. 2 schematically represents a lung airway skeletonization, according to some embodiments of the present disclosure.

Brief reference is now made to FIG. 2, which schematically represents a lung airway skeletonization 200, according to some embodiments of the present disclosure. The skeletonization 200 is rendered with thickness (black region 201) and centerlines (light lines 202 along the centers of the black segments).

Returning to FIG. 1: At block 112, in some embodiments, deformation parameters are defined for the tree graph. Through these parameters, flexibility is given to the model. The tree graph deformation parameters are defined per bifurcation node of the skeletonized, but not necessarily for all such nodes in the tree graph. In some embodiments, the nodes are defined for branch orders of up to about 3 or 4 levels. Nodes may be defined for higher levels as appropriate, e.g., along a pathway which is traversed by an interventional instrument.

In some embodiments, each bifurcation of the skeleton is assigned a coordinate system, described by a 4×4 3-D rigid transformation matrix $T_i$ from local bifurcation coordinates to CT coordinates (or in any other suitable coordinates). Alternatively, the coordinate system may be described by a 4-D quaternion and a 3-D position, or by another suitable method.

Figure 3:
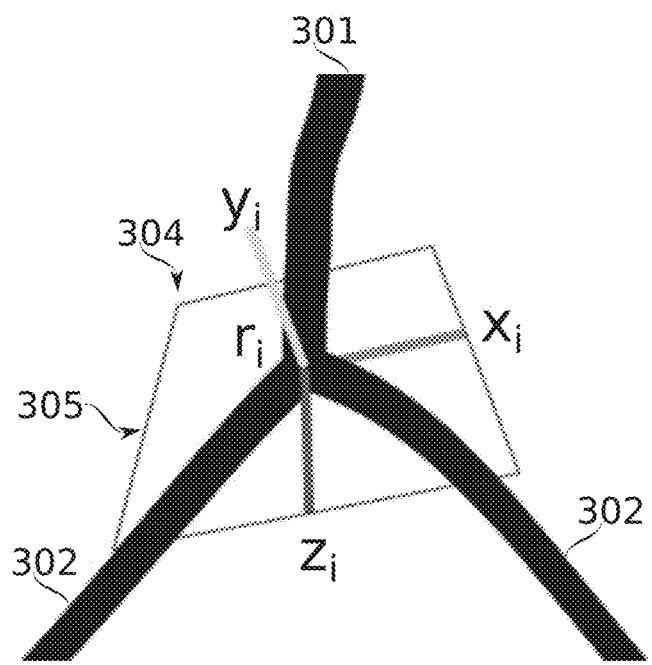
FIG. 3 schematically represents bifurcation coordinate system (also referred to herein as coordinate system $T_i$) and bifurcation plane, according to some embodiments of the present disclosure.

Reference is made to FIG. 3, which schematically represents bifurcation coordinate system 304 (also referred to herein as coordinate system $T_i$) and bifurcation plane 305, according to some embodiments of the present disclosure. Parent airway 301 leads from the trachea, and splits into sub-branch airways 302.

The coordinate system 304 is positioned, for example, at the vertex of bifurcation $r_i$, with its Y axis $y_i$ perpendicular to the plane of bifurcation 305. The plane of bifurcation 305 is defined, in some embodiments, as the plane which both contains the bifurcation point $r_i$ and is optimally aligned with all the airway branches connected to the bifurcation. Its Z axis $z_i$ may be defined to point along the direction of the airway which ends at $r_i$, and also forced to lie on the bifurcation plane such that $z_i \perp y_i$. The remaining X axis may then be defined as $x_i = y_i \times z_i$ to form a right-handed coordinate system.

In addition, the first (root) vertex in the tree is also assigned a coordinate system $T_0$ in which the Z axis points in the direction of the beginning of the trachea. The Y axis may be chosen arbitrarily, but can be chosen for simplicity as the closest vector perpendicular to Z and aligned with Y of the end of the trachea.

The specific construction of coordinate systems $\{T_i\}$ with its special choice of orientation as described above is convenient for representing each bifurcation, but the deformation model is invariant to the specific construction and can use any coordinate systems centered at the bifurcations, or, more generally, which reflects the deformation state of branches and bifurcations.

Each 3-D transform $T_i$ can be represented by the position vector $r_i$ and 3 Euler angles $(\alpha,\beta,\gamma)$, position vector and a 3×3 rotation matrix $R_i$, as well as position vector and a 4-D quaternion $q_i$. The set of all coordinate systems $\{T_i\}$ forms a hierarchy of transformations. In order to represent a deformation of the airways map, the suggested model uses the bifurcations as control points (or joints). It describes the deformation applied to the bifurcations and computes the deformation inside the airways using interpolation methods. Let $U_i = T_{p(i)}^{-1} T_i$ where $p(i)$ is the parent bifurcation of $i$ (or the root of the tree) and define $U_0 = T_0$. $U_i$ represents the i-th bifurcation coordinate system in its parent bifurcation coordinates. One can then write a chain multiplication rule for $\{T_i\}$: $T_i = U_0 \ldots U_{p(p(i))} U_{p(i)} U_i$ that is, a product of all relative transformations between a bifurcation and its parent bifurcation, from the i-th bifurcation up to the root node. By applying a deformation on $U_i$, all descendant bifurcations are also affected in a tree-like manner.

Figure 4:
FIG. 4 schematically illustrates a lung airway skeleton before (left side) and after (right side) deformation between bifurcations and, according to some embodiments of the present disclosure.

Reference is now made to FIG. 4, which schematically illustrates a lung airway skeleton before (left side 410) and after (right side 411) deformation between bifurcations 402 and 401, according to some embodiments of the present disclosure. The deformation alters positioning at bifurcation 401 and all its descendants by applying a rotation $\Delta U_i = R_\omega$ to the corresponding $U_i$. Other bifurcations indicated specifically include bifurcation 403, which is not affected by the deformation.

Applying a deformation using $U_i$ also affects all descendants of the modified bifurcation 401. This may be plausible in most cases of a deformation applied to the lungs. For example, in the case of a single lung being slightly rotated relative to the other, this can be reflected by rotating a single $U_i$, e.g., as illustrated in FIG. 4.

In some cases, it may be desirable to apply a deformation to a single bifurcation only, without affecting its descendants. This can be easily achieved by modifying the corresponding $T_i$ directly. However, in the following description deformation is applied using $U_i$, as the inventors have found by experimentation that the tree-like behavior better captures the nature of deformation of the lungs. Moreover, the change can be encoded with many fewer parameters. Changes to remaining intersections $\{T_i\}$ are then computed by the chain multiplication rule described above.

Denoted by $U_{i,0}$ is the original bifurcation transform relative to its parent (which can be the initial state from the CT or from an initial deformation computation). By $U_{i,t}$ is denoted the deformed bifurcation transform at time t.

To model a lung deformation, $U_i$ may be modified by applying deformation transforms $U_{i,t}$ to bifurcation coordinate systems represented in the state of left-hand side 410 of FIG. 4 in the following manner: $U_{i,t} = \Delta U_{i,t} U_{i,0}$. $\Delta U_{i,t}$ then describes the deformation in parent coordinates. If $\Delta U_{i,t} = I_4$ (the identity matrix) then no deformation is applied to the i-th bifurcation (relative to the initial state). However, if for example $\Delta U_{i,t} = R_\omega$ (a rotation matrix of $|\omega|$ degrees around rotation axis $\omega$) then $U_{i,t}$ deforms the i-th bifurcation (and all its descendants) by rotating it by $\omega$ relative to $p(i)$, as depicted in FIG. 4.

Applying the deformation using $\Delta U_{i,t}$ in parent bifurcation coordinates, and forcing the deformation to a zero or small offset, produces a deformation model in which the distances between the bifurcations and the angles between branches are almost entirely preserved. The deformation is applied to the model along the length of the airways without affecting the overall distances and angles at the bifurcations, as illustrated in FIG. 4. $\Delta U_{i,t}$ can then be described using 3 Euler angles, if offsets are not allowed, or with a total of 6 parameters if offsets are to be allowed.

In some embodiments, interpolation of points inside branches is done in the following manner: $v_i(\sigma): [0,1] \to \mathbb{R}^3$ represents a curve describing the initial shape of the i-th branch, which starts at bifurcation $p(i)$ and ends at bifurcation $i$ (there exists a one-to-one correspondence between bifurcations and branches by considering for each bifurcation the branch ending at the bifurcation). $v_i(\sigma)$ is given in CT coordinates. $v_i(0) = r_{p(i)}$ represents the initial location of bifurcation $p(i)$ and $v_i(1) = r_i$ represents the initial location of bifurcation $i$.

Given deformed bifurcation transforms $\{T_{i,t}\}$, $v_{i,t}(\sigma)$ is to be computed, which represents the deformed curve of the i-th branch in deformed CT coordinates at time t. Denoted by $\Delta T_{i,t} = T_{i,t} T_{i,0}^{-1}$ is the deformation of the i-th bifurcation from CT to deformed CT coordinates at time t.

According with these definitions, the following interpolation formula is applied, in some embodiments:

$$v_{i,t}(\sigma)=\text{interp}(\Delta T_{p(i),t},\Delta T_{i,t},\sigma)(v_i(\sigma))$$

Where interp can be any interpolation function between two 3-D rigid transforms. For example, interp can split the transforms into a rotation and translation and treat each part separately. Interpolation of rotations can be achieved using SLERP (Spherical Linear Interpolation) of quaternions or any other suitable method, while interpolation of translations can be done by a simple weighted average.

It may be verified that $v_{i,t}(0)=r_{p(i),t}$, the deformed location of the p(i)-th bifurcation; and that $v_{i,t}(1)=r_{i,t}$, the deformed location of the i-th bifurcation. This shows that the interpolation formula treats the start and end points of the branch curve as expected.

Summing up, the deformation model described in relation to FIGS. 1-4 assign coordinate systems to bifurcations of a skeletonized lung airway model, each bifurcation being represented as $\{T_i\}$. It then describes the deformed bifurcations at time t using $\{T_{i,t}\}$. The bifurcations can be arranged in a tree-like hierarchy and computed using a chain multiplication rule using transforms $\{U_i\}$ and their deformed counterparts $\{U_{i,t}\}$. $\Delta U_{i,t}$ provides a convenient representation for deformation of bifurcations in their parent bifurcation coordinates.

Having deformed the bifurcations, branch curves are interpolated accordingly using the bifurcations at their start and end points. Using just a few parameters, the model describes most of the natural deformations which occur in the lung during NB procedures. The model can be applied for the use of real-time dynamic deformation tracking as well as breathing compensation as will be shown below.

Deformable Registration

Figure 5:
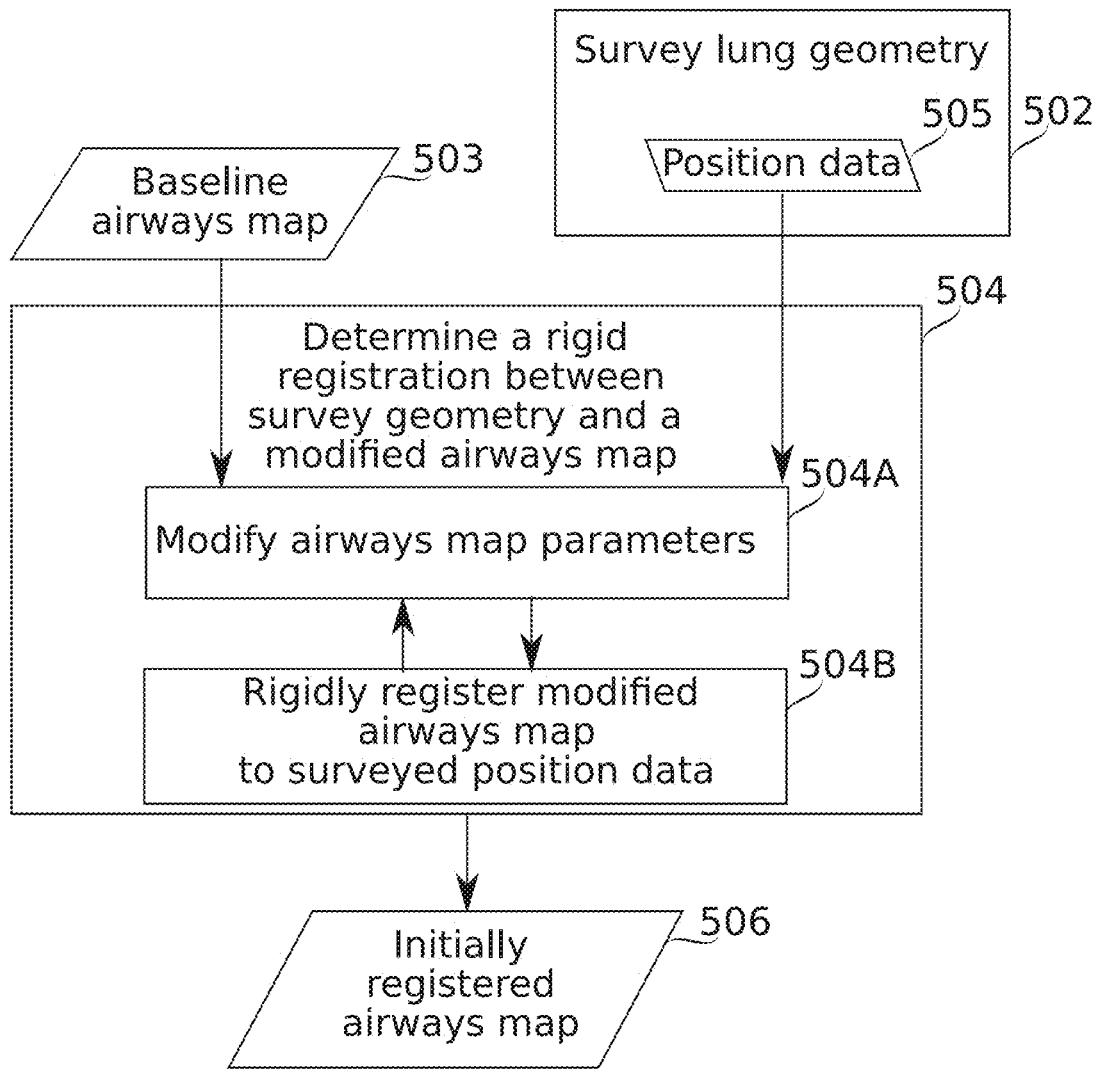
FIG. 5 is a schematic flowchart representing a method of performing a deformable registration between the position of a catheter positioned in lung airways and a branched model of the airways, according to some embodiments of the present disclosure.

Reference is now made to FIG. 5, which is a schematic flowchart representing a method of performing a deformable registration between the position of an interventional instrument positioned in lung airways and a branched model of the airways, according to some embodiments of the present disclosure.

At block 502, in some embodiments, the physician performs an unsupervised survey using one or more single-sensor or fully tracked interventional instruments, as described above. The samples are captured in LOC coordinates, with their location inside the anatomy unknown and to be determined by the process of registration. Position data 505 generated by the survey is made available to the operations of block 504, and in particular block 504A.

Baseline airways map 503 is structured with an at least partial representation of some previously measured geometry of the lungs, generated, for example, as described in relation to FIG. 1. Although the lungs surveyed in block 502 and represented by baseline airways map 503 are the same lungs, there may have been changes in geometry between the time of acquisition of the data of baseline airways map 503, and the survey of block 502.

At block 504, in some embodiments, a rigid registration is determined between the unsupervised survey data and the airways map (as generated from prior imaging, e.g., using CT). Block 504 is divided into blocks 504A and 504B, which may be performed concurrently or sequentially, and optionally iteratively. In block 504A, modifications to the airways map are made to improve its similarity to a current anatomical state. Block 504B represents rigid registration (e.g., translation and rotation).

Algorithms for the registration of block 504B are known in the art. They perform determination of the rigid registration using energy minimization optimization methods, usually starting from an unsupervised survey performed with a single sensor. However, without additional modification (as provided for in block 504A), the airways map generated from the preoperative CT may not accurately reflect the anatomy at the time of the procedure: there is most likely a deformation between the airways map of the preoperative CT and the lung state during the actual procedure. Potential reasons for this include, for example: the preoperative CT (or other preoperative imaging procedure) is usually taken days or even weeks before the procedure; the patient is examined in a posture changed relative to the CT scan (or other baseline imaging procedure); and/or forces exerted on the lung by a bronchoscope or other endoscope, catheter, tools used therewith, and/or similar surgical instruments modify its shape.

Accordingly, in some embodiments of the present disclosure, additional operations, represented by block 504A, adjust the deformation model to make it more suitable for finding a rigid registration between LOC and anatomy. The anatomy is initially represented by a deformable model with a "null" deformation model applied, relative to the CT (and representing, as baseline airways map 503, the state of the lungs during the CT). During registration, the deformation model is modified by a deformation selected to compensate for changes in the state of the lungs between the time of the CT or other 3-D imaging, and the time of the NB procedure.

Block 506 represents an initially registered state of the deformation model (airways map) which may continue to change during a procedure as the lungs undergo further dynamic changes.

In some embodiments of the present disclosure, selection of changes to airway map parameters (deformation) used in block 504A is based on position and orientation sensing data acquired from one or more fully tracked interventional instruments positioned and/or moving within the lung. Position data from the tracking is provided to block 504A from block 505. Compared, e.g., to interventional instruments tracked only at the tip, a fully tracked interventional instrument provides more data, and in particular, data more directly indicative of the longitudinal extent of the interventional instrument's position in the current moment (e.g., timestamp).

Since the lung is moving during the procedure, the interpretation of old position data can be ambiguous or misleading, making it less useful than data which unambiguously indicate the current position of all or most of the interventional instrument. As an indication of the type of problem that can arise with older data: once the lung moves, the assumption that the interventional instrument position indicated in the older data is still within the original airway is invalid (and at least doubtful). To correct this, some information of how the lung has moved is needed. But with tip-only tracking, there is no sensor in position to provide that information. With a fully tracked interventional instrument, on the other hand, the moving position of portions of the interventional instrument proximal to the tip can be relied on to faithfully represent the moving position of the airway itself. Furthermore, the tie between older data and newer data is clear, since the interventional instrument itself makes a kind of constant "ruler". Accordingly, comparing older and newer data can directly indicate what type of lung motion may have occurred.

Figure 6:
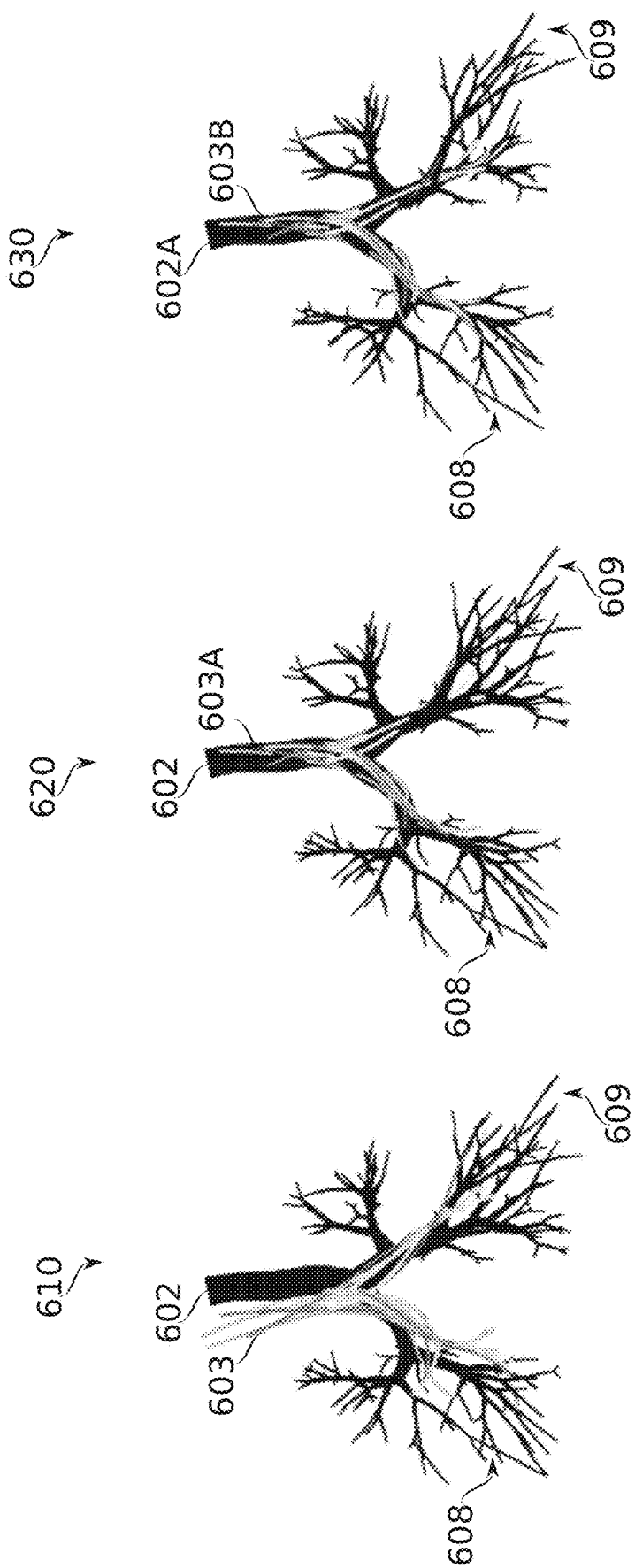
FIG. 6 schematically represents lung model states, differently registered with survey data, according to some embodiments of the present disclosure.

Brief reference is now made to FIG. 6, which schematically represents lung model states 602, 602A with survey data differently registered as registered survey data 603, 603A, 603B according to some embodiments of the present disclosure. In this example, the samples of the survey data 603 were gathered using a fully-tracked interventional instrument. In the transition from state 602 to state 602A, regions 608 and 609 (for example) have changed their positions relative to the rest of the lung model.

Panel 610 (left) shows original survey positions 603 roughly overlaid onto lung model 602, resulting a large degree of misalignment with survey data 603. Panel 620 (middle) shows the result of a rigid registration of survey data 603A to lung model 602. This is like the result of performing block 504B without previous processing of the model through block 504A. It results in errors, particularly in the more distal portions of the lung. Panel 630 (right), shows a lung model 602A which has been transformed by deformation guided by the survey data 603B, correcting the rigid registration errors seen in panel 620.

Returning to discussion of FIG. 5: In some embodiments of the present disclosure, the baseline airways map 503 is built as an instance of the deformation model described in relation to FIG. 1. In order to capture both deformation and rigid registration between LOC and anatomy, it is convenient for the sake of registration to think of $\{T_i\}$ as bifurcation coordinate systems in LOC coordinates. In this sense, $U_0 = T_0$ encodes the rigid transform from anatomy to LOC (of the root node) while $\{U_i\}_{i>0}$ represent the local transformation and deformation in between bifurcations, as before. This single model encodes both rigid anatomy-to-LOC registration ($U_0$) as well as local CT deformation.

In some embodiments, the optimization process of block 504 is configured to fit a model that will (a) place all gathered interventional instrument LOC-samples inside the deformed and transformed airways (essentially, to perform the operations of block 504B) and (b) describe a reasonable deformation of the lungs which allows this (the operations of block 504A). These two conditions—target goal and shape constraints—are optionally encoded in a single energy function. Alternatively, fitting is performed using a plurality of energy functions in iterative alternation.

To prevent over-fitting and to make the convergence more robust, bifurcations of generation greater than a certain threshold (for example, greater than the third generation) are optionally omitted from the model. Optionally, one or more of the greater bifurcation generations is included in fit calculations only after initial fitting with lower-generation bifurcations has converged to a solution. The interventional instrument position measurements (samples gathered by the survey) are optionally preprocessed or assigned weights to make them balanced in their contribution to the fitting.

For encoding the rigid portion of the transform between the locally deformed airways map in CT coordinates to LOC coordinates there may be assigned $U_0$ in 6 parameters (6-DOF). This is used as part of the operations of block 504B. Optionally, parameter values are confined to a restricted (reasonable) search area. In some embodiments, $U_0$ is searched in an initial global search step, as done in other algorithms of this sort. Relative scaling of position data 505 and baseline airways map 503 may be well characterized from the conditions of data acquisition; optionally, a scaling factor is included in the transform fitting.

Figure 7A:
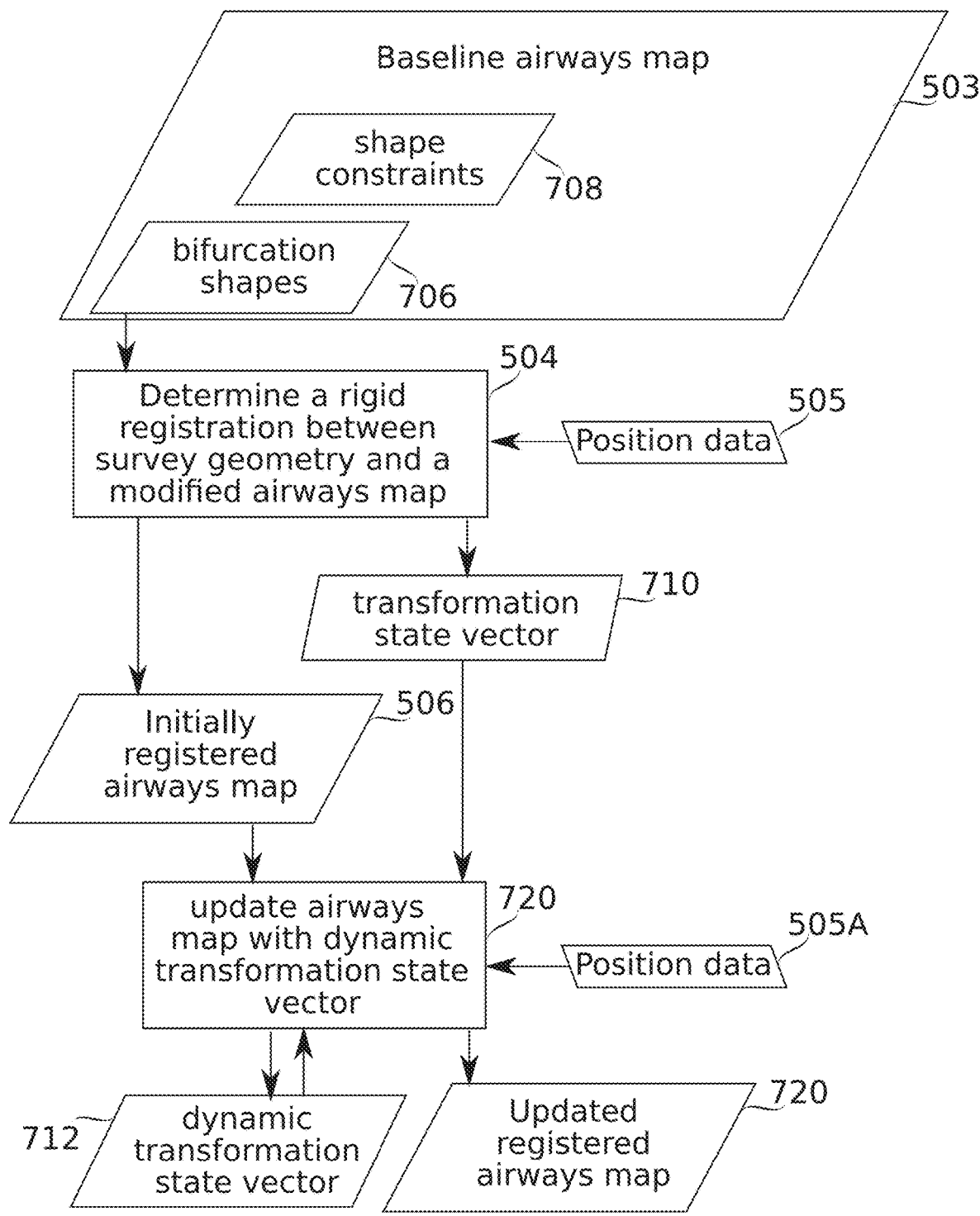
FIG. 7A schematically represents elements of the determination of a deformation transformation of a deformation model to match available data, and use of the deformation transformation in further dynamic modeling according to some embodiments of the present disclosure.

Reference is now made to FIG. 7A, which schematically represents elements of the determination of a deformation transformation of a deformation model to match available data, and use of the deformation transformation in further dynamic modeling according to some embodiments of the present disclosure. The descriptions with respect to FIG. 7A outline a more particular embodiment for some of the operations of FIG. 5, and add blocks showing how the results of that embodiment may be further used to model dynamic changes in the lung during a procedure.

In some embodiments, local deformation (e.g., as performed by operations of block 504A) is performed on the baseline airways map (block 503, as also shown in FIG. 5) by $\{\Delta U_i\}_{i>0}$. Optionally, this is defined with only 3-DOF (if offsets are not allowed) or 6-DOF (if offsets are allowed). The model's parameters can be assembled in a single state vector $x = (U_0, \Delta U_1, \Delta U_2, \ldots, \Delta U_N)$ where the matrices are to be represented in their compact 3-DOF or 6-DOF form and $i = 0, 1, \ldots, N$ are the bifurcations participating in the optimization process.

Block 706 represents bifurcation-assigned shapes, in the form of at least the rotation states assumed in the model by the branches of the bifurcation. Block 708 represents shape constraints. Optionally these constraints defined per bifurcation to limit and/or guide how the shapes of block 706 can be modified. For the i-th bifurcation (i>0), shape constraints can be encoded simply by using the following energy function: $E_{shape}^i(\Delta U_i) = \Delta U_i - I_4 \in \mathbb{R}^{16}$. This restricts the optimization to finding only small and local deformations between bifurcations. Optionally, shape constraints are specified in another way, for example, via application of a machine-learned set of scoring weights to a particular model configuration to score its energy function.

$E_{shape}^i$ can moreover be assigned a weight depending on the generation of the bifurcation or on its characteristic radius which makes it more or less susceptible to distortion by the fitting process. For example, the main carina can be made stiffer relative to deeper bifurcations of smaller radius.

The definition of $E_{shape}^i$ above includes a simplification by mixing between a rotation matrix and a translation of arbitrary units. Alternatively, in some embodiments, $\Delta U_i$ is split into a 3×3 rotation matrix R, and a translation vector $t = (x, y, z)$. Each can be compared with $I_3$ and 0 respectively and each difference assigned its own weight.

Alternative to considering $R - I_3$: in some embodiments the rotation is expressed and analyzed in its quaternion form $q = q_w + iq_x + jq_y + kq_z$. The shape energy function would then correspondingly read $E_{shape}^i(\Delta U_i) = W_{gen}^i \cdot (W_t^i \cdot (x, y, z), W_q \cdot (q_x, q_y, q_z)) \in \mathbb{R}^6$, forcing $(q_x, q_y, q_z)$ towards 0, that is, zero rotation. Optionally, different types of rotations are distinguished in $\Delta U_i$. This can also be achieved, for example, by analyzing q and assigning it different weights for different kinds of rotations (for example, making model segments easier to bend at the bifurcation but more difficult to twist). For embodying this distinction, the specific construction of the coordinate systems $\{T_i\}$ described in relation to FIG. 1 is potentially well suited. Optionally, fit weighting is selected to prefer offsets in a certain direction and/or discourage offsets in other directions. From these examples, it can be appreciated that the implementation of $E_{shape}^i$ may take any of several different forms imposing shape constraints on the deformation applied to a specific bifurcation to reflect realistic lung deformation configuration.

The optimization process is indifferent to the choice of specific energy function. The total shape energy function is then:

$$E_{shape}(x) = (E_{shape}^1(\Delta U_1), E_{shape}^2(\Delta U_2), \ldots, E_{shape}^N(\Delta U_N))$$

For joint fulfilling the two goals of block 504, i.e., finding the rigid transform (block 504B) and local deformation (block 504A) such that the position data 505 (e.g., from gathered interventional instrument samples during survey movements of the interventional instrument) are inside the deformed and transformed airways, there are considered, in some embodiments, distances between the gathered interventional instrument samples on one side, and on the other side, the deformed and transformed airway tubes (in LOC coordinates).

When a sample from position data 505 sits well inside an airway tube defined by an airways map (baseline airways map 503, or another airways map after modification), then it shouldn't contribute any error to the optimization. However, if a sample is located outside the bounds defined by the branching airways model, then the model and/or the rigid registration should be corrected as to minimize this error.

Denoted by $\{S_k\}_{k=1}^{K}$ are the gathered interventional instrument position samples of position data 505, converted by 4×4 3-D transforms from local interventional instrument or sensor coordinates into localization coordinates LOC. Alternatively, the interventional instrument position samples are described as a 4-D quaternion and a 3-D position vector or in any other suitable representation.

Variations on the use of gathered interventional instrument position samples are optionally implemented according to the type of interventional instrument position data available. Implemented with a 5-DOF tracking system, for example, the $1^{st}$ and $2^{nd}$ axes of the rotation matrix in each $S_i$ may be absent. Implemented for use with a single-sensor interventional instrument, each $S_i$ represents the interventional instrument's tip at some time during the registration survey. With a full interventional instrument localization system, the full interventional instrument length is continuously visible. In this case, $S_k$ may be generated by breaking the fully tracked interventional instrument into a series of discrete transforms along its length (e.g., using spline or other interpolation methods), to generate many $S_k$'s at each moment (time stamp). The optimization process as such is indifferent to the structure of the interventional instrument position measurement (single-sensor vs. fully tracked) as well as to the number of tracked interventional instruments. It only requires a set of $\{S_k\}$ as input. Denoted by $s_k$ is the translation (position) vector of each $S_k$. For a given sample $S_k$, the sample energy is defined as follows:

$$E_{smp}^{k}(x)=W_k \Gamma(s_k, \text{Skel}(x)) \in \mathbb{R}$$

Where $W_k$ is a weight assigned to the specific k-th sample, Skel(x) represents the airways map skeleton deformed by deformation model state vector x, as described in detail in Section (3) and $\Gamma(v, \text{Skel})$ is a function which outputs the shortest distance or offset between a position vector v and a skeleton model Skel. When x represents the true deformation and transformation, $E_{smp}^{k}(x)$ is expected to be 0 for each k. $W_k$ can be chosen in various ways. For example, with a fully-tracked interventional instrument, at each timestamp the full interventional instrument is broken into multiple discrete $\{S_k\}$'s. Their corresponding $W_k$ can assign for example stronger weight for the tip of the interventional instrument relative to its tail, to make the optimization focus on deeper airways when searching for the deformable registration. For the choice of $\Gamma$ one can use a simple distance function between v and the deformed skeleton Skel(x), but then the optimization will try to fit all gathered samples into the centerlines of the skeleton, which is not necessarily the case. In order to avoid this the radii of the deformed skeleton need to be taken into account. A normalized distance function may be used which finds the closest normalized (dimensionless) distance by dividing distances by their corresponding radius from the closest point on the skeleton; normalized distances are then measured in 1-radius, 2-radius instead of [mm], [cm] etc. One can then consider a normalized distance less than 1 as a point being inside an airway. Therefore, the radius-normalized distance can undergo a transfer function such as SmoothReLU with an offset to consider all radius-normalized distances below 1 as nearly 0 and grow linearly for radius-normalized distances greater than 1. The optimization will still see some small errors for off-center samples, but they will be negligible. More generally, one may define $E_{smp}^{k}(x)=\Gamma(S_k,\text{Skel}(x))$ where $\Gamma$ now sees the full 3-D transform $(S_k)$ of the $k^{th}$ sample, and finds the shortest distance between the full 3-D transform and the deformed skeleton. This formulation allows $\Gamma$ to include orientation distance between an interventional instrument sample and the deformed tree, requiring, for instance, that the direction of the interventional instrument will be aligned with the direction of the closest skeleton point. In addition, instead of just outputting the shortest normalized distance between an interventional instrument sample and the deformed tree, $\Gamma$ may output a full difference vector in 3-D, or 2 difference vectors in 3-D—one for the position and another for orientation. It should be appreciated that the optimization is indifferent to the specific choice of $\Gamma$ and $E_{smp}^{k}$, they should only be chosen such that airways will be attracted to samples, preferably with a normalization depending on airway radii and with nearly uniform cost inside airway tubes. The total samples energy function is then:

$$E_{smp}(x)=(E_{smp}^{1}(x), E_{smp}^{2}(x), \ldots, E_{smp}^{K}(x))$$

And the total energy function is:

$$E(x)=(W_{smp}E_{smp}(x), W_{shape}E_{shape}(x))$$

Where $W_{smp}$ and $W_{shape}$ provide the balance between deforming airways to samples and satisfying shape constraints and are chosen by experimentation. E(x) is represented as a multidimensional errors vector, each component of which describing a certain specific type of error. The goal for the optimization process is to find state vector x which minimizes the total error $\|E(x)\|$. Optimization can be done using various non-linear methods, such as Gradient-Descent, Nelder-Mead, Trust Region, Levenberg-Marquardt (LM) etc. Some optimization methods (such as LM) exploit the representation of the error function as a multidimensional vector of errors to speed up and increase the robustness of their convergence process. For example, LM optimization uses the Jacobian of the errors vector E(x) for its convergence. The Jacobian of E(x) can be computed numerically or analytically and be used in LM or other types of non-linear optimization algorithms.

The output of the deformable registration process is a state vector x (block 710) which describes the parameters of a transformation and deformation model $\{\Delta U_i\}_{i \geq 0}$ which can be used as the initial state for a NB procedure. With a fully tracked interventional instrument, potentially enough samples may be collected to fit a flexible deformable model on the gathered interventional instrument samples, gaining fit improvements, e.g., as described in relation to FIG. 6.

Dynamic Deformation Tracking

The deformable registration of FIG. 7A outputs a set $\{\Delta U_i^{reg}\}$ (transformation state vector 710) which encodes the rigid transformation from anatomy to LOC ($\Delta U_0^{reg}$) as well as the local deformation of the CT in its initial state ($\Delta U_i^{reg}$ i>0). During an NB procedure, the baseline airways map is transformed/deformed to reflect an updated (e.g., present and real-time) state of the airways map 720 in LOC coordinates.

In some embodiments, updated registered airways map 720 is described by $\Delta U_{i,t} = \Delta U_{i,t}^{dyn} \Delta U_i^{reg}$; that is, the total transformation and deformation of block 710 is applied to the baseline airways map 503, along with an additional dynamic transformation state vector 712 which encodes dynamic changes. In more detail: the static part ($\Delta U_i^{reg}$) comes from the deformable registration and describes the airways map transformation at the initial deformed state in the procedure. The dynamic part ($\Delta U_{i,t}^{dyn}$) updates dynamically during a procedure to account for dynamic forces which deform the lungs.

In some embodiments, breathing deformation is excluded from $\Delta U_{i,t}^{dyn}$, and instead integrated into $\Delta U_i^{reg}$ (for example, as discussed in the section on breathing deformation).

At the beginning of the NB procedure, after production of initially registered airways map 506, $\Delta U_i^{dyn} = I_4$ and $U_{i,0}^{dyn} = \Delta U_i^{reg} U_{i,0} = U_{i,t}^{reg}$, that is, baseline airways map 503 is transformed just by transformation state vector 710. Additional deformation is added to the model by combination with the existing $\Delta U_i^{reg}$. One can also write $U_{i,t}^{dyn} = \Delta U_{i,t}^{dyn} U_i^{reg}$ to indicate starting with $\{U_i^{reg}\}$ and deforming it locally over time during the procedure.

The dynamic deformation tracking algorithm implemented by the operations of block 720 is similar to the deformable registration implemented by the operations of block 504.

At each of a plurality of times t, a new set of interventional instrument samples supplied as position and orientation data 505A is available $\{S_k\}_{k=1}^K$.

In the case of a single-sensor interventional instrument, K=1. For a fully tracked interventional instrument many $S_k$'s may be given; for example, by sampling each sensor along the interventional instrument, and/or by further breaking the representation of the interventional instrument into a series of discrete transforms along its length using spline or other interpolation methods.

Similarly to the initial deformable registration producing initially registered airways map 506, the deformation tracking algorithm of block 720 is indifferent to the number of interventional instruments used as well as to each interventional instrument's configuration. The dynamic deformation tracking algorithm of block 720 is configured to update the deformation model by computing $\Delta U_{i,t}^{dyn}$, such that for each time t, most samples from position data 505A will be inside airways and such that the applied deformation would describe a plausible lung deformation as above. In some embodiments, this comprises jointly minimizing the two types of "energy" defined by the aggregate distances of samples from the airways, and by the implausibility of a certain configuration, for example as constrained by shape constraints used by block 720 which are like shape constraints 708 used by block 504.

Relative to the deformable registration algorithm implemented by block 504, however, the deformation tracker of block 720 does not have as many interventional instrument samples in its disposal.

In some embodiments, deformation tracking only uses the current full interventional instrument's position at present time t. In some embodiments, deformation tracking also uses past samples from position data 505; for example, by adding them to $\{S_k\}$ with weights decreasing as the data ages.

It is an object of some embodiments of the present invention to provide continuously updated deformation tracking at a fast (real-time) rate, and low latency. This object is in part assisted by updating the deformation model incrementally to match new data from position data 505A as it is acquired. This incremental updating is consistent with the object of low latency, to the extent that the lungs' actual rate of deformation is relatively slow compared to the sampling rate of position data 505A.

In some embodiments, the deformation tracker of block 720 reuses the definition of energy functions from the deformable registration of block 504 to define the energy of the dynamic deformation part of the model:

$$E_{shape}^{dyn}(x_t) = (E_{shape}^1(\Delta U_{1,t}^{dyn}), E_{shape}^2(\Delta U_{2,t}^{dyn}), \ldots, E_{shape}^N(\Delta U_{N,t}^{dyn}))$$

$$E_{smp}^{dyn}(x_t) = (E_{smp}^1(x_t, x_{reg}), E_{smp}^2(x_t, x_{reg}), \ldots, E_{smp}^K(x_t, x_{reg}))$$

$$E^{dyn}(x_t) = (W_{smp} \cdot E_{smp}^{dyn}(x_t), W_{shape} \cdot E_{shape}^{dyn}(x_t))$$

Where:

$x_t$ is the model's state vector at time t, now including only the dynamic part: $x_t = (\Delta U_{1,t}^{dyn}, \Delta U_{2,t}^{dyn}, \ldots, \Delta U_{N,t}^{dyn})$, $x_{reg}$ is the deformable registration's state vector, $E_{shape}^{dyn}(x_t)$ is the shape energy function, optionally focused now only on the dynamic part—that is, it does not punish for the registration's shape, only for the additional dynamic shape (although, alternatively, initial shape may be taken into account), and $E_{smp}^{dyn}(x_t)$ is the samples' energy function that is a measure of the distance between the interventional instrument samples and the final transformed and deformed skeleton (including registration and dynamic deformation).

The dynamic deformation tracker, in some embodiments, assumes that the shape coming from the deformable registration is true—that is, it does not include it in its shape energy function. It only searches for local deformation corrections $\Delta U_{i,t}^{dyn}$ that will approximate the interventional instrument's samples and will not deviate much in shape relative to the original shape defined by the deformable registration performed at block 504.

Insofar as the information per iteration available to the dynamic deformation tracking algorithm is limited, there is a risk of over-fitting. In any case, convergence and runtime should occur quickly in order to maintain real-time updates.

In some embodiments, meeting these criteria is assisted by restricting the attention of the tracker algorithm implemented at block 720 to bifurcations which are close to the interventional instrument.

For example, supposing that a tracked interventional instrument is located inside the right lung, deformation of bifurcations in the left lung in an attempt to minimize $\|E^{dyn}(x_t)\|$ will be fruitless, since it can have no significant effect on the total energy.

In some embodiments, the optimizer used when recalculating the dynamic transformation state vector 712 only modifies bifurcations in $x_t$ which can potentially affect the energy function, that is, bifurcations in sufficient proximity to the tracked interventional instrument(s). These may include bifurcations that the interventional instrument currently traverses, optionally along with bifurcations selected according to some metric of distance, e.g., branch distance and/or distance in space.

Again similarly to some embodiments of the deformable registration algorithm implemented at block 504, $x_t$ may be limited to bifurcations up to a certain generation. Bifurcations are optionally given a weight for optimization in $E_{smp}^i(x_t)$, based, for example, on generation or characteristic radius.

The $\Gamma$ distance function used to match interventional instrument sample positions to the transformed and deformed skeleton Skel($x_t, x_{reg}$) so that $E_{smp}^{dyn}(x_t)$ can be computed is potentially computationally expensive. To avoid consideration of the entire tree, irrelevant (e.g., distant from the interventional instrument sample position) parts of the tree may be omitted from the search to gain some speedup. This can be implemented, for example, by restricting consideration to skeleton points which are within a certain radius from the interventional instrument samples, and forming a sub-skeleton with them and all their ancestors for the Γ distance computation.

Figure 7B:
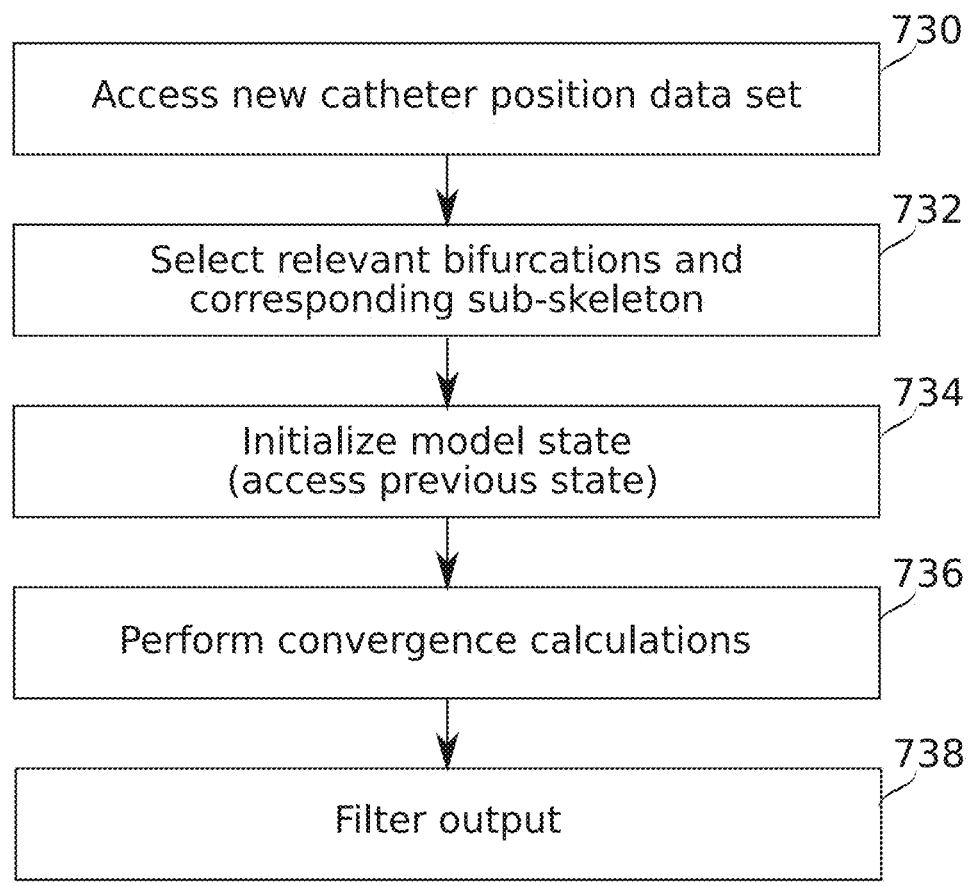
FIG. 7B is a flowchart that schematically illustrates an embodiment of block of FIG. 7A, according to some embodiments of the present disclosure.

Reference is now made to FIG. 7B, which is a flowchart that schematically illustrates an embodiment of block 720 of FIG. 7A, according to some embodiments of the present disclosure. Operations of FIG. 7B are performed iteratively as interventional instrument position data is continuously acquired, to maintain an updated model of the lung during a procedure.

At block 730, in some embodiments, the deformation tracker accesses a new set of interventional instrument samples $\{S_k\}$ and weights $W_k$. The weights may be adjusted, for example, to give stronger weights to the distal tip of the interventional instrument compared to its more proximal portions.

At block 732, in some embodiments, the tracker then chooses a set of bifurcations and a relevant sub-skeleton for optimization based on proximity to $\{S_k\}$.

At block 734, in some embodiments, a model state vector is initialized with its state from the previous iteration $t_0: x_t = x_{t_0}$.

At block 736, in some embodiments, one or more convergence steps are performed, for example, using a nonlinear iterative optimization method such as the Levenberg-Marquardt (LM) algorithm, updating $x_t$ to minimize the error function $\|E^{dyn}(x_t)\|$. The number of convergence steps may be selected to avoid overuse of available computational resources. It may be quite low—even just one step. Since the real-time operation of the algorithm helps to ensure that there should be no significant changes between sampling times, the model should normally be close to its convergent state in any case.

At block 738, in some embodiments, the resulting $x_t$ is optionally filtered to force the tracker to a smoother response; for example by using:

$$\Delta U_{i,t}^{dyn} \leftarrow \text{interp}(\Delta U_{i,t_0}^{dyn}, \Delta U_{i,t}^{dyn}, 1-\alpha)$$

with $\alpha$ controlling the amount of filtering to be performed between deformation states of previous and new timestamps $t_0$ and t (0—no filter, immediate update, 1—full filter, no update).

Additionally or alternatively, dynamic deformation is restricted by use of an optional damping stage applied after each update step: $\Delta U_{i,t}^{dyn} \leftarrow \text{interp}(\Delta U_{i,t}^{dyn}, I_4, \beta)$ where β controls the amount of damping to be performed (0—no damping, full update, 1—full damping, no update). By adding damping (β>0) the dynamic deformation always relaxes and goes back to zero. It is only in the case that the interventional instrument samples $\{S_k\}$ indicate a local deformation compared to the deformable registration that the deformation tracker will maintain a non-vanishing local deformation transforms $\Delta U_{i,t}^{dyn}$.

It should be noted that the shape energy function $E_{shape}^{dyn}$ may also implicitly push the dynamic deformation towards the identity matrices $I_4$ unless $E_{smp}^{dyn}$ gives resistance, but the explicit damping stage can assist to accelerate and better control the damping process.

Remaining remarks in this section relate to details of the error minimization calculations of block 736.

By performing local convergence steps only, there is a risk of the algorithm becoming trapped at a local minimum of $E^{dyn}(x_t)$ from which local convergence algorithms such as LM will not be able to easily recover.

This can happen, for example, when the interventional instrument is located near a deep and highly deformed bifurcation, and/or a bifurcation, the deformation of which was not modeled during the deformable registration step.

From such a bifurcation, it may not be absolutely clear, initially, if the interventional instrument takes the right or left turn at the bifurcation. In the example described next, it is supposed that an interventional instrument takes the right turn at an ambiguously modeled bifurcation. A potential advantage of a fully tracked interventional instrument in combination with the deformation model described herein is that after entering a certain airway and traveling a short distance the shape of the interventional instrument itself teaches the system whether the interventional instrument turned right or left, even under significant deformation. After the right turn, for example, $\|E^{dyn}(x_{right})\| < \|E^{dyn}(x_{left})\|$ where $x_{right}$, $x_{left}$ represent the state vectors of a dynamic deformation which accounts for a right or left turn respectively. However, since the deformation tracking algorithm is local in nature, $x_t$ might falsely converge towards $x_{left}$ during navigation, falsely forcing the left airway to align with the interventional instrument by applying the suitable (excessive) dynamic deformation.

After the interventional instrument travels a short distance inside the airway, the option of $x_{left}$ becomes definitely inferior to $x_{right}$, but it may be too late then for a local convergence algorithm to go all the way back, escape from the local minimum $x_{left}$ and converge to the global minimum $x_{right}$.

In some embodiments of the present disclosure, a global search is incorporated in the dynamic deformation tracking algorithm which may allow escaping from local minima.

One example of a global search implementation applies a search (e.g., a random or grid search) near the current state vector $x_t$ in the form of small perturbations $\{x_t + v_i\}_{i=1}^M$ where $v_i$ modifies $x_t$ in certain directions in an attempt to find a state vector with a smaller total error. The error function of each perturbation $v_i$ can be evaluated in parallel in a search algorithm that can easily utilize multiple computation processing units such as a graphics processing unit (GPU).

Another option uses a multiple hypothesis approach. At a specific bifurcation, the skeleton may be split in two sub-skeletons: one containing the left turn and all its descendants (but not containing the right turn) and the other containing the right turn and all its descendants (but not containing the left turn). The tracker runs two separate optimizations, one using the "left" skeleton and the other using the "right" skeleton in $E_{smp}^{dyn}(x_t)$. The optimizer using the "right" skeleton will be forced to converge to the right turn, since the left turn is missing from the sub-skeleton. At the beginning the "left" optimizer may show smaller error; however, after the interventional instrument travels a short distance, the "right" optimizer will win and the "left" hypothesis will be dropped.

Formalizing this approach: for each iteration time t, skeleton paths $\{P_j\}$ are searched which are within a certain distance from the interventional instrument samples $\{S_k\}$. It may be assumed that the interventional instrument must fit into one of those paths. Local convergence is then run in order to find $x_j$ that minimizes $\|E^{dyn}(x, P_j)\|$ (here $E_{smp}^{dyn}$ uses $P_j$ in its Γ distance function). Each $x_j$ describes the model's state vector which minimizes the energy function based on the assumption that the interventional instrument is located inside path $P_j$.

Denoted by $E_j=\|E^{dyn}(x_j,P_j)\|$ is the error at the minimum state vectors $x_j$. $j_0$ can then be chosen such that $E_{j_0}=\min\{E_j\}$. If $E_{j_0}<\|E^{dyn}(x_t)\|$ then it means that the optimizer found a state vector which improves the locally converging $x_t$ and the optimizer may choose to set $x_t\leftarrow x_j$ and thus escape from a local minimum point. This global multi-hypothesis search can run on each dynamic deformation tracking step. Alternatively, each hypothesis can be tested on a separate step to reduce the computation power required. The intuition behind this idea is the following:

$$E^{dyn}(x_t) \approx \min_j\{E^{dyn}(x_t, P_j)\}.$$

This implies that though the convergence surface defined by $E^{dyn}(x_t)$ may contain many local minima (the accumulation of all local minima of each $E^{dyn}(x_t,P_j)$), each of these $P_j$-specific convergence surfaces is itself much simpler and so easier to search.

Similarly to the deformable registration, the dynamic deformation tracking algorithm may be formalized in terms of an error minimization optimization problem. The total dynamic deformation error function $\|E^{dyn}(x_t)\|$ forms a complex convergence surface. The solver may employ global minimization, a multi-seed approach (several starting points), a multi-hypothesis approach, or any other suitable local/global method for real-time minimization of the error function while avoiding local minima. $x_t$ can be filtered over time to create a continuously updating dynamic deformation experience, and can be damped in order to accelerate convergence ("relaxation" back to the initial deformable registration state.

Together with the deformable registration, the total deformation transform described by $\Delta U_{i,t}=\Delta U_{i,t}^{dyn}\Delta U_i^{reg}$ accounts for both deformation and transform between the preoperative CT and the anatomy at the beginning of the procedure (in LOC coordinates), and additional dynamic deformation of the lungs during NB procedure. One major difference between the deformable registration algorithm and the dynamic deformation tracker is in that the deformable registration sees many interventional instrument samples and produces a single deformation and transformation state $x_{reg}$ which may take several seconds to compute; while the dynamic deformation tracker is real-time and provides rapidly evolving $x_t$'s based on just a few observed $S_k$'s on each timestamp.

Breathing Deformation

In some embodiments of the present disclosure, the rigid registration determined at block 504 of FIGS. 5 and 7A is a cyclically-varying registration. More particularly, in some embodiments, the registration varies according to movements of the breathing cycle.

A problem in NB procedures is overcoming the deformation and inaccuracy caused by breathing. Such motion may be particularly significant for peripheral targets in the lung, more remote from the relatively anchored and/or stiff structures of the trachea and large bronchi.

An approach to addressing this problem uses reference sensors attached to the patient's chest to create generalized LOC coordinates which move with the body and chest. Breathing-induced movement of lung and interventional instrument is compensated for to some extent using changes in the reference sensor locations, as the two motions tend to correlate.

However, lung deformation due to breathing is complicated. For example, one airway may deform in one direction while another airway deforms in the opposite direction. This can reduce accuracy of simple reference sensor-based breathing compensation algorithms.

In partial compensation for such complications, reference sensor readings may be interpreted in view of respiratory phase. For example, breathing phase $\phi\in[0,1]$ may be calculated from the periodic motions of the reference sensors. Phase may be expressed, for example, as a number between 0 and 1 where $\phi=0$ signifies full exhalation state and $\phi=1$ signifies full inhalation state. In this representation, the breathing phase oscillates between these two extremes. Alternatively, $\phi$ may be understood as a true phase on a circle ($\phi\in\mathbb{T}^1$), where $\phi=0\approx1$ may signify full exhale state and $\phi=0.5$ signifies full inhale state. Treating $\phi$ as a phase on a circle allows distinguishing between the exhale-to-inhale transition motion and the inhale-to-exhale transition motion, which do not necessarily follow the same motion pattern as a function of references sensor outputs.

Having computed the breathing phase, a function correlating between breathing motion and breathing phase may be applied. In outline, the function accepts breathing phase as a parameter predictive of an output which estimates breathing motion at a certain interventional instrument's location. The function may, for example, use a breathing model tailored to the patient's motions; learned by imaging and/or measurements made offline (prior to the interventional instrument navigation procedure) and/or during the NB procedure.

By applying the function in real-time, breathing motion of the interventional instrument can be compensated for, e.g., by making it static with respect to a static airways map, despite that both the interventional instrument and the mapped airways are actually deforming with breathing. However, if the lung deforms such that it no longer matches the periodic predictions of the breathing model, motion compensation will degrade.

In some embodiments of the present disclosure, the anatomy and interventional instrument are displayed dynamically as the interventional instrument navigates though the lung; and in their measured and/or estimated true shape/position states, including deformations due to breathing or other causes. Accordingly, breathing motion of the interventional instrument is retained, rather than eliminated by the use of corrections.

In some embodiments, to model the breathing, a breathing phase $\phi$ is calculated, for example, based on one or multiple reference sensors attached to the patient's chest. The breathing phase may be computed using standard signal processing methods, based, for example, on up-and-down motions of the tracked reference sensor correlating with the patient's periodic breathing motion. At the highest sensor position the patient is estimated to be in full inhalation state; at the lowest sensor position it is estimated that the patient is in full exhalation state.

A high-pass filter may be used to filter out the patient's other body movements. Additionally or alternatively, multiple reference sensors may be employed, with each sensor's location may be computed in sensors' PCA coordinates. In some embodiments, instead of using a reference sensor's absolute or relative height, an area, for example of a triangle between 3 reference sensors may be examined. For example, it may be assumed that the patient is in full inhalation state when the area of this triangle is maximal and in full exhalation when the area of the triangle is minimal. The breathing phase ϕ may be computed in a method similar to one of the techniques describe above or by any other suitable method.

In some embodiments of the present disclosure, ϕ is used in the initial deformable registration stage (e.g., operations of block 504 of FIG. 5). Replacing a single deformable registration state $x_{reg}$ which reflects the lungs' deformation state at the beginning of the procedure, with a time-varying registration accounting for deformations of the lungs in accordance with breathing phase ϕ. Accordingly, the deformable registration algorithm is modified to find a ϕ-dependent initial deformable registration of the lungs $x_{reg}^\phi$. From this result, the system can later predict in real-time lungs deformations due to breathing. The system's total correction will be $\Delta U_{i,t} = \Delta U_i^{dyn} \Delta U_{i,\phi}^{reg}$—that is, a dependence of the initial registration on breathing phase ϕ is introduced.

The dynamic deformation tracker of, e.g., block 720 of FIG. 7A uses as its input from block 506 $\Delta U_{i,\phi}^{reg}$, in place of $\Delta U_i^{reg}$. The dynamic deformation tracker can compute a differences from the phase-compensated registration $\Delta U_{i,\phi^{reg}}$ just as it would for $\Delta U_i^{reg}$, though potentially with less error. Filtering, e.g., as described in relation to block 738 need not be tuned to allow passing breathing cycle motions, potentially improving the algorithm's artifact rejection characteristics.

Even without any interventional instrument present inside the airways, the breathing phase is optionally computed using the one or multiple reference sensors attached to the patient, allowing the airways map to continue "breathing", in-sync with the patient's true breathing.

In some embodiments using breathing phase ϕ∈[0,1]: $x_{reg}^\phi$ is calculated from measurements of the extrema states $x_{reg}^{\phi=0}$ and $x_{reg}^{\phi=1}$, one deformable registration state for exhale and one for inhale, respectively. Between these measured states, other states are interpolated: $x_{reg}^\phi$=interp($x_{reg}^{\phi=0}, x_{reg}^{\phi=1}, \phi$). This interpolates between "exhalation" and "inhalation" states using the breathing phase ϕ. The extrema states are optionally calculated from results of a single registration survey, separating measurements made at either extreme into different data sets.

In some embodiments, definitions of the deformable registration state vector and the energy functions are modified to be defined as follows:

$$x_{reg} = (x_{reg}^{\phi=0}, x_{reg}^{\phi=1})$$

$$E_{reg}^{shape}(x_{reg}) = (E_{reg}^{shape}(x_{reg}^{\phi=0}), E_{reg}^{shape}(x_{reg}^{\phi=1}))$$

$$E_{smp}(x_{reg}) = (E_{smp}^1(x_{reg}^{\phi 1}), E_{smp}^2(x_{reg}^{\phi 2}), \ldots, R_{smp}^K(x_{reg}^{\phi K}))$$

The state vector now incorporates both models: exhalation and inhalation. The shape energy function is optionally modified such that both models impose similar shape constraints.

For further customization, each model can be assigned different shape constraints or at least be weighted differently. For example, weighting may be based on knowledge that the preoperative CT was taken in full inhale state, so that there is expected to be a more significant deformation in the "exhalation" model compared to the "inhalation" model. The weighted correction is handled, for example, by introduction of the phase-varying term $E_{smp}$.

Instead of matching each interventional instrument sample with a single deformable model $x_{reg}$, each sample is matched to a breathing skeleton with breathing phase $\phi_k$ where $\phi_k$ is the breathing phase belonging to interventional instrument sample $S_k$. More formally:

$$E_{smp}^k(x_{reg}^{\phi k}) = W_k \Gamma(S_k, \text{Skel}(x_{reg}^{\phi k}))$$

This attracts both models $x_{reg}^{\phi=0}, x_{reg}^{\phi=1}$ towards the interventional instrument samples, where samples taken with ϕ≈0 mostly affect the "exhalation" model, samples taken with ϕ≈1 mostly affect the "inhalation" model and samples with ϕ well inside [0,1] affect both.

To fit the two models onto the gathered interventional instrument samples $\{S_k\}$, the number of samples K available should diversely sample from the range of $\{\phi_k\}$. In some embodiments, the controlling system is configured to make sure that enough samples of enough diversity are collected from both lungs and from all breathing phases to prevent over-fitting. This is made potentially much easier with a fully tracked interventional instrument, due to the large number of interventional instrument sample collected for each timestamp.

It should be noted that the two key-phase breathing model is optionally extended to any number of breathing key phases. For example, one may define: $x_{reg} = (x_{reg}^{\phi=0}, x_{reg}^{\phi=0.5}, x_{reg}^{\phi=1})$ in which case 3 registration states are used to describe 3 corresponding breathing key phases: exhalation, exhalation-inhalation, and inhalation. Interpolation is then done between 3 key phases: $x_{reg}^\phi$=interp($x_{reg}^{\phi=0}, x_{reg}^{\phi=0.5}, x_{reg}^{\phi=1}, \phi$) and the energy functions are defined as before. For a full breathing phase on a circle (ϕ∈ $\mathbb{T}^1$) at least 3 breathing key phases are preferably used to model the full breathing cycle. For a simple phase (ϕ∈[0,1]) two key phases are potentially sufficient ($\phi_0=0, \phi_1=1$). Adding more breathing key phases may increase the accuracy of the breathing model, but might also cause over-fitting in the breathing model, if not enough interventional instrument samples are present.

Although $x_{reg}^\phi$ models most breathing motion, there may be a remaining unmodeled breathing deformation error left due to inaccuracy of the proposed exhalation-inhalation interpolation model. The dynamic deformation tracker can eliminate at least some of this residual error using its $\Delta U_{i,t}^{dyn}$. Accuracy of the deformable breathing registration model is important for providing the dynamic deformation tracker with a good starting point for local deformation searching, and/or for use in modeling the breathing of the lungs regardless of whether there is an interventional instrument inserted to the lungs, by just relying on the breathing phase. The dynamic deformation tracker can then just focus on finding relatively smaller and/or slower developing deformations near $x_{reg}^\phi$ by imposing stronger shape constraints in $E_{shape}^{dyn}$. This can improve its overall performance.

Deformation and Breathing Views

Figure 8A:
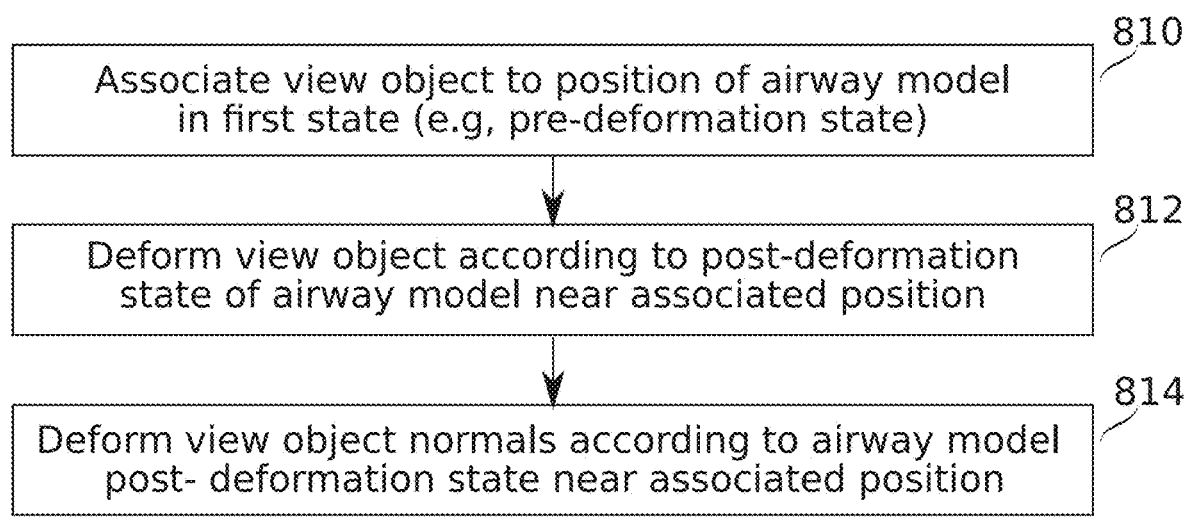
FIG. 8A is a schematic flowchart outlining a method of generating deformable lung model views, according to some embodiments of the present disclosure.

In some embodiments of the present disclosure, a system is configured to show views of a deformable lungs model, optionally together with a view illustrating the positions of one or more interventional instruments positioned within the lungs modeled by the deformable lungs model. Reference is now made to FIG. 8A, which is a schematic flowchart outlining a method of generating deformable lung model views, according to some embodiments of the present disclosure.

A 3-D mesh describing a smooth boundary surface of the airways segmentation may be used to represent the airways map for use during navigational bronchoscopy. A 3-D mesh consists of a set of vertices and triangular faces which connect them to form a surface. Optionally, the airways 3-D mesh is generated in a skinning process directly from the airways skeleton (centerlines and radii) to form a "synthetic" 3-D mesh representing the airways map. Additionally or alternatively, gradient information taken directly from the CT volume or from the segmented airways volume is used to capture the fine texture of the airways. This potentially generates a more "realistic" mesh.

In some embodiments of the present invention, a current deformed state of a deformable lungs model is preferably applied to views of any of the lung-associated 2-D/3-D features (view objects) displayed by the system (that is, not only the model's skeleton). This has the potential advantage of showing the anatomy realistically in its real-time state.

Examples of such view objects include, for example: the airways 3-D mesh, a target representation such as a sphere or realistic target mesh, pathways through the lung, waypoints within the lung, and/or CT slices imaging the lung.

Turning now to block 810 of FIG. 8A: in some embodiments of the present disclosure, determination of deformed-state positioning of a view object begins with association of the view object to the airways of the skeleton of the deformable lungs model.

In some embodiments, this is association comprises assigning one or more vertices of the displayed object (defined in a pre-distortion space, for example, the space of the original CT image used to define the model skeleton) to a respective airway and normalized distance $\sigma \in [0,1]$ along the airway. In the case of the 3-D airways mesh, for example, each vertex of the mesh originates from a certain skeleton branch at a certain distance $\sigma$ along that branch. The 3-D mesh may be broken into a hierarchy of branches, identical to the hierarchy of the airways skeleton, where each sub-mesh corresponds to a certain branch of the skeleton and each vertex on a branch has a $\sigma$ value assigned to it.

At block 812, in some embodiments, the 3-D mesh (or other representation of the view object) is deformed by applying on each vertex v a corresponding interpolation transform using the deformation model $\{T_i\}$. For example:

$$v_{deform} = \text{interp}(\Delta T_{p(i),t}, \Delta T_{i,t}, \sigma)(v)$$

Where v in CT (or other 3-D image) coordinates belongs to the i-th branch with distance $\sigma$ along that branch, p(i) is the parent branch of i and $\Delta T_{i,t}$, $\Delta T_{p(i),t}$ are the deformations of the bifurcations at the beginning and end of the branch, respectively.

Optionally, at block 814, a lighting model used to render the deformed 3-D mesh is improved (e.g., reducing the appearance of faceting) by applied a similar deformation on the vertex normals:

$$n_{deform} = \text{interp}(\Delta R_{p(i),t}, \Delta R_{i,t}, \sigma)(n)$$

Where n is the normal vector corresponding to vertex v and $\Delta R_{i,t}, \Delta R_{p(i),t}$ are the corresponding rotation matrices of transforms $\Delta T_{i,t}, \Delta T_{p(i),t}$, ignoring offsets.

Optionally the deformations of blocks 812, 814 are applied by a central processing unit (CPU), transforming all vertices (and normals) using their suitable deformation transforms. Optionally the deformations are applied by a graphics processing unit (GPU) for example using a 3-D shader. A shader is a program running on the GPU for each specific section of the graphics pipeline. A vertex shader program is responsible for processing each vertex in the graphics pipeline and can be used for changing the geometry of objects before they're displayed.

Breaking the 3-D mesh into a hierarchy of branches (sub-meshes) assists applying the deformation model using a vertex shader. Before drawing each branch (sub-mesh) the vertex shader is given the matrices $\Delta T_{i,t}, \Delta T_{p(i),t}$. A draw command is then issued containing the branch geometry information (vertices, normals, texture coordinates etc.). The $\sigma$ distances along the branch are given as additional per-vertex data, for example, using an unused texture coordinates channel, such that they're made accessible to the vertex shader program. Inside the shader program a vertex is inputted together with its $\sigma$ distance. Using the preconfigured $\Delta T_{i,t}, \Delta T_{p(i),t}$ the interpolated deformation transform is computed for the specific vertex and applied on the vertex position and normal. The deformation model can also be applied using general GPU computing toolboxes such as CUDA or in any other suitable method.

In order to apply the deformation model on a small object, such as a 3-D target sphere, guidance arrows, texts etc. it is observed that the deformation model is smooth and does not change much in small neighborhoods. The small object may therefore be assumed to undergo a uniform deformation transform. To apply the deformation model, the small object is assigned a specific branch from the airways map (for example, the closest branch) and a constant $\sigma$ distance which indicates its distance (or its center-of-mass distance) along the branch. Its vertices (and normals) are then deformed as described above.

Figure 8B:
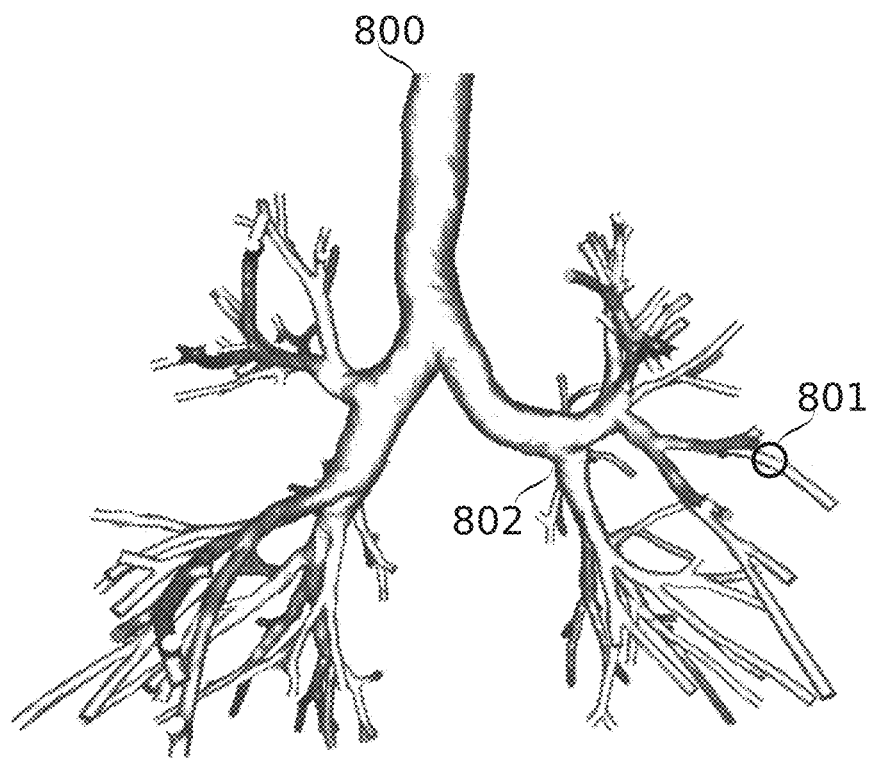
FIGS. 8B-8C schematically represent renderings of -D mesh before and after deformation of a single model bifurcation and its descendants, according to some embodiments of the present disclosure.
Figure 8C:
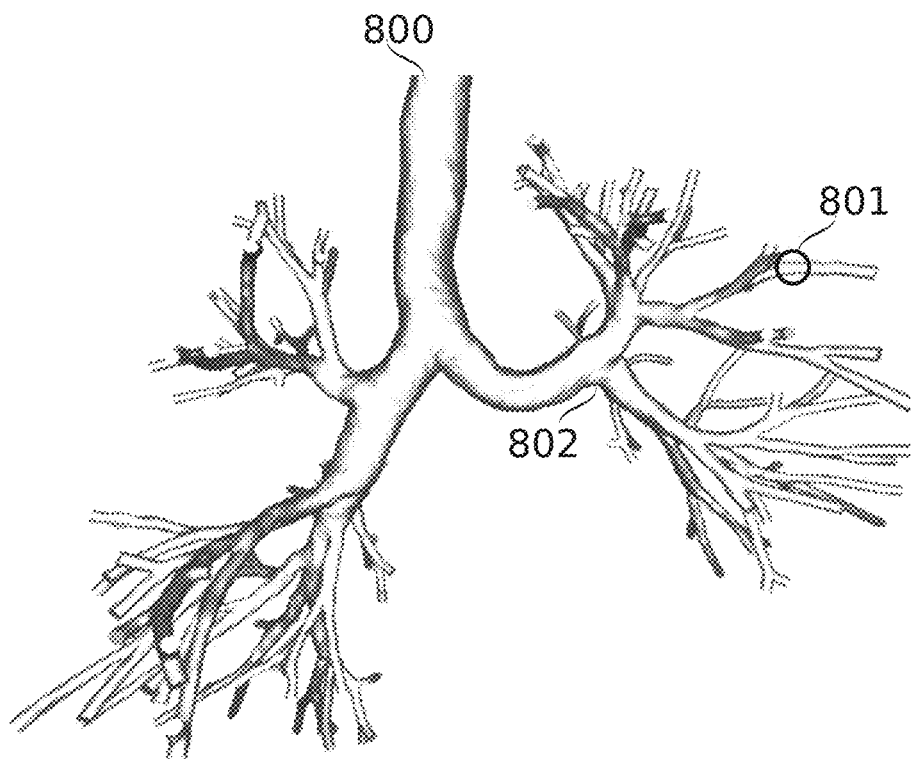

Reference is now made to FIGS. 8B-8C, which schematically represent renderings of 3-D mesh 800 before and after deformation of a single model bifurcation 802 and its descendants, according to some embodiments of the present disclosure. Also shown is an indication of a target 801.

The deformation applied to convert the model underlying FIG. 8B to the model underlying FIG. 8C is the same single-bifurcation deformation of bifurcation 802 as shown for FIG. 4. However, the deformation is now applied on vertices of the 3-D mesh (and normals) as described above, to display a smooth deformed 3-D mesh. The parameter adjustment is to the bifurcation itself. The appearance of an increased bend in FIG. 8C results from interpolation of the airway between the changed configuration at bifurcation 802, and the bifurcation more proximal to it. The interpolation used can be a uniform curve, but it need not be; for example, stiffness is constrained, in some embodiments to be higher near the more proximal bifurcation, where the airway is larger, and/or where the airway wall is thicker. When available, position measurements from an interventional instrument through the airway region linking two bifurcations can additionally or alternatively be used as a constraint. Curvatures are optionally constrained by the curvature present in the baseline state of the lungs.

Target 801 illustrates a small (e.g., about 1 cm diameter) target deformed via its assignation to a certain branch with a corresponding $\sigma$ distance. Sometimes it may seem that multiple airways can be assigned to a single small object; for example, in cases where a small 3-D target is positioned at a bifurcation or even above the skeleton. In this case it may not matter much which branch to choose for binding the small object with the skeleton; because the deformation model is smooth and $\sigma$ is used, the deformation interpolation formula would yield similar results for different (close) assignments of airways. However, when an object is located far from the airways map, for example, if a target is very peripheral compared to the segmented airways or a full CT slice is to be deformed, then a more elaborate deformation extrapolation technique needs to be performed, as described below. In another situation, a target object may be primarily associated with a non-lung structure (e.g., the ribcage), with the lung being used as an access-way. In this case in particular, it is important to have good absolute representational accuracy of the lung's position, since it cannot be relied on that the target will move along with the airways near it.

In other situations, the target's deformed position may be predicted based on the deformable tracked airways. This is optionally implemented by using a trained model (e.g. a final elements model) which predicts how deformation propagates through tissue (as represented by the CT or MRI scan). In this case, the target will not be associated with an airway, nor with any other specific anatomical structure. Instead, its position will be deformed by propagating the airways' tracked deformation towards the target's surrounding tissue.

The deformation model describes how bifurcations deform using a set of deformation transformations $\{T_i\}$. These transforms can be interpolated along branches to describe how each point on the curved centerline of an airway deforms according to the model. Points which are not exactly on the centerlines but close enough (for example, within two radii of an airway) can be assumed to deform the same way as their closest centerline points. However, it is relatively not easy to tell how a point which is located far from any airway deforms, based on the deformation of airways. For example, a feature implemented in some embodiments of the present disclosure comprises displaying a CT slice containing the current interventional instrument's location inside the lungs, in a dedicated or combined view (together with the airways map). In some embodiments of the deformation tracking algorithm, the NB system displays anatomical features in their real position in space, and this optionally includes the display of a suitably deformed CT slice. Without deforming the CT slice, the voxel data in the slice will reflect the state of the anatomy prior to the procedure without any deformation applied (and be out of alignment with other displayed objects).

The problem of extending the deformation model from the airways to regions outside of them is a problem of extrapolation. The deformation model is known at certain positions in 3-D space and needs to be extended outside to other points. The extrapolation can be achieved, for example, by using Thin-Plate-Spline (TPS) or another radial basis function (RBF) more generally, or general basis methods. Additionally or alternatively, a machine learning method may be applied which predicts based on training on a training set of examples the most probable deformation propagation within the lung tissue; and/or a finite-elements simulation model is used to predict the propagation of deformation through the tissue, as represented by the CT or MRI scan.

In some embodiments, for example, a set of base functions (for example TPS) is trained on the known control points of the deformation model such that it sends bifurcation or even full-length centerline points to their known destinations (according to the deformation model). The extrapolation model uses basis functions which can then be sampled anywhere. Since they approximate the known control points to a good accuracy, it is assumed that they will send outside points (which do not belong to airways) to plausible destination locations as well. These models can be combined with a smoothness measure which is suitable for the lungs.

Another example of an extrapolation method uses a K-nearest neighbors (KNN) approach: A point p which is not located inside an airway is to be deformed. Then p is searched for its K-nearest neighbor points from the non-deformed skeleton, which are denoted by $v_k$ with weights $w_k$ using their distances. For example: $w_k = \text{dist}(p, v_k)^{-P}$ with P>0, giving a stronger weight to neighbors close to p. By increasing P the closest point becomes more dominant relative to the others. Using the K-nearest neighbors and their weights, one can then compute a deformation offset for p as follows:

$$\Delta p = \frac{\sum_{k=1}^{K} w_k \Delta v_k}{\sum_{k=1}^{K} w_k}$$

Alternatively, one can compute a full deformation transform at p by using a variation of the interp function which is able to compute a weighted average of multiple transforms $\{T_i\}$.

Instead of using a simple extrapolation approach which is only based on smoothly extending control points, a more elaborate deformation extrapolation can be implemented. For example, insofar as the ribs do not deform substantially during NB procedures, they can be assumed to be static. This information can be added to the extrapolation function in terms of additional control points: one can generate points on the surface of the segmented ribcage and force those points to stay static in the deformation. This provides a boundary condition to the extrapolation function, forcing it to decay as it comes closer to the ribcage. Alternatively, the lung are modeled not only using their airways but also using blood-vessels, fissures, pleura and other anatomical features. These features can then be fed into a skeletal model (similar to the deformation model above) and used to predict total lung deformation based on a few known control points, in methods similar to those mentioned above. In some embodiments, the physics of the lungs are simulated; for example, by applying a finite-elements simulation, thus providing better predictions for the deformation of the lungs in between control points. In some embodiments, trained machine-learning models are used to predict the propagation (or extrapolation) of the deformation from known control points to other lung tissue; for example, replacing conventional finite-element simulations with understandings derived from observed lung tissue behavior.

Figure 9A:
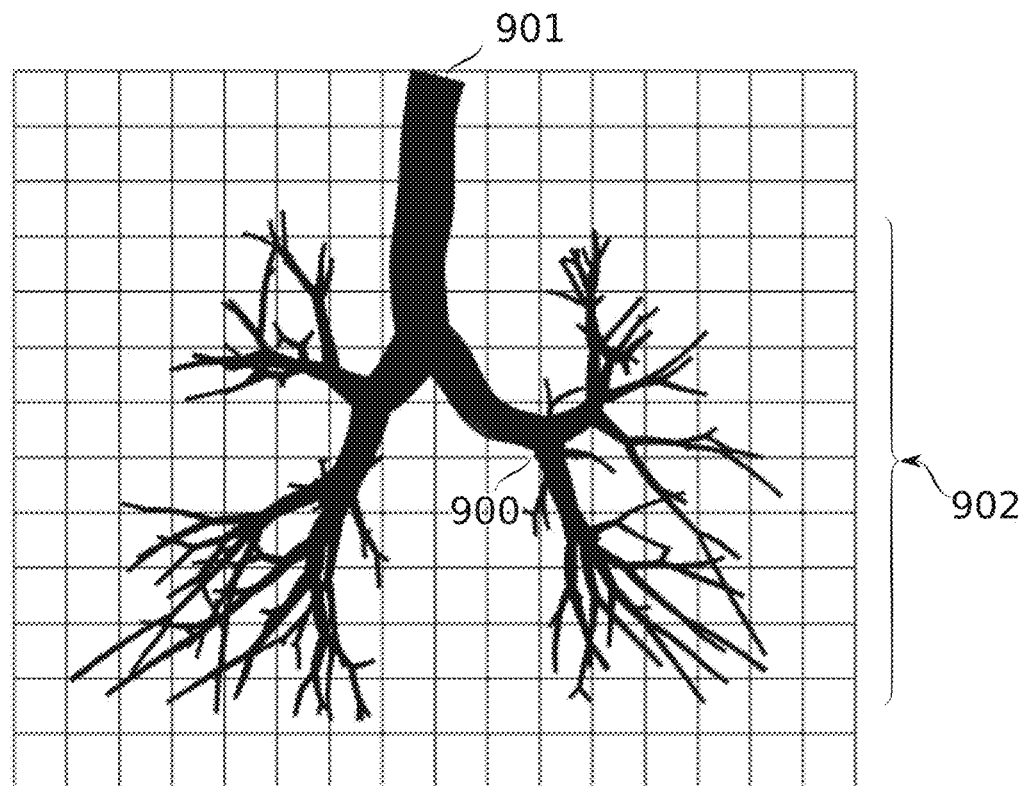
FIGS. 9A-9B schematically illustrate a x slice interpolation grid before (FIG. 9A) and after (FIG. 9B) deformation of a single bifurcation and all its descendants, according to some embodiments of the present disclosure.
Figure 9B:
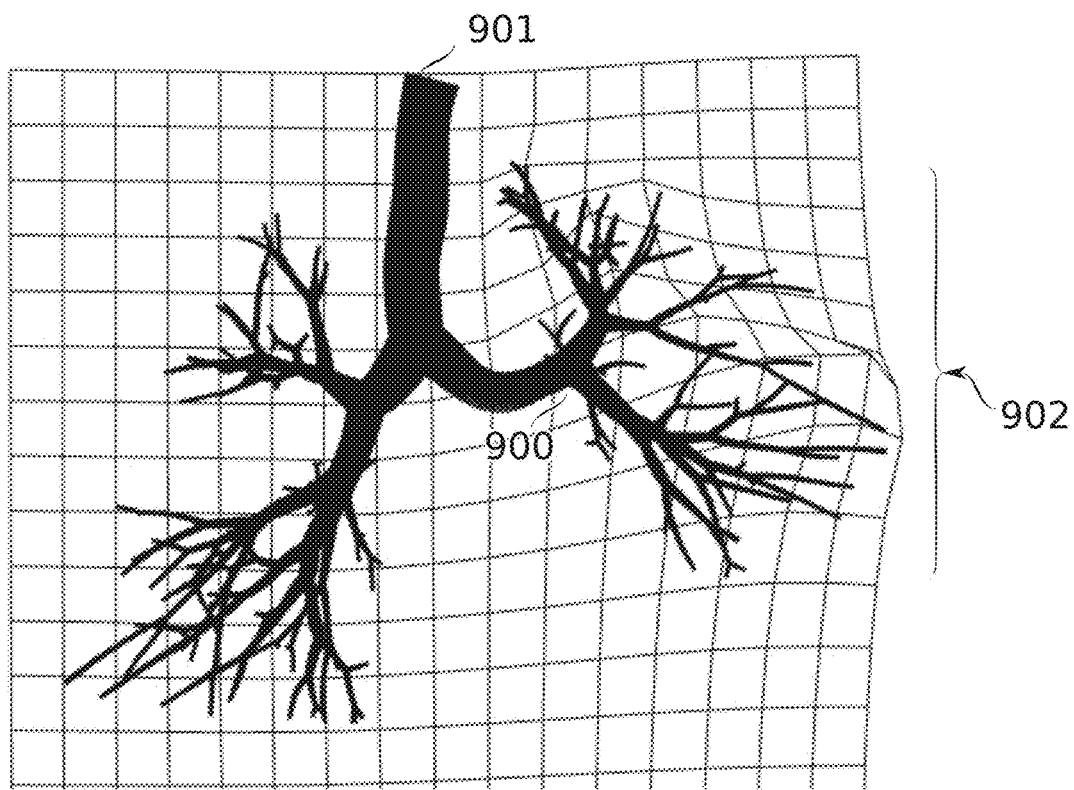

Reference is now made to FIGS. 9A-9B, which schematically illustrate a 16×16 slice interpolation grid before (FIG. 9A) and after (FIG. 9B) deformation of a single bifurcation and all its descendants, according to some embodiments of the present disclosure. Bifurcation 900 of skeleton 901 is deformed in FIG. 9B, resulting also in the movement of lung region 902.

Deforming a full CT slice each voxel in the CT slice optionally uses one of the extrapolation methods mentioned above. However, this can be computationally expensive, since a CT slice usually contains a large number of voxels (for example, 512×512), and the extrapolation formulas are rather computationally involved. Deformation of a CT slice may be simplified by constructing a low-resolution uniform grid consisting, for example, of 16×16 blocks covering the entire CT slice. The deformation is computed at each corner point and the deformation in between grid points is then computed by simple interpolation using the neighboring corner points, for example, using 2-D bilinear interpolation, bi-cubic interpolation, spline interpolation, or any other suitable method. Using interpolation methods rather than direct per-pixel deformation computation is greatly preferable in terms of computation resources, and is almost as accurate as the direct deformation approach due to the reasonable smoothness of the deformation model. When a finer result is required then a denser grid can be used (for example, 32×32 blocks).

Figure 9C:
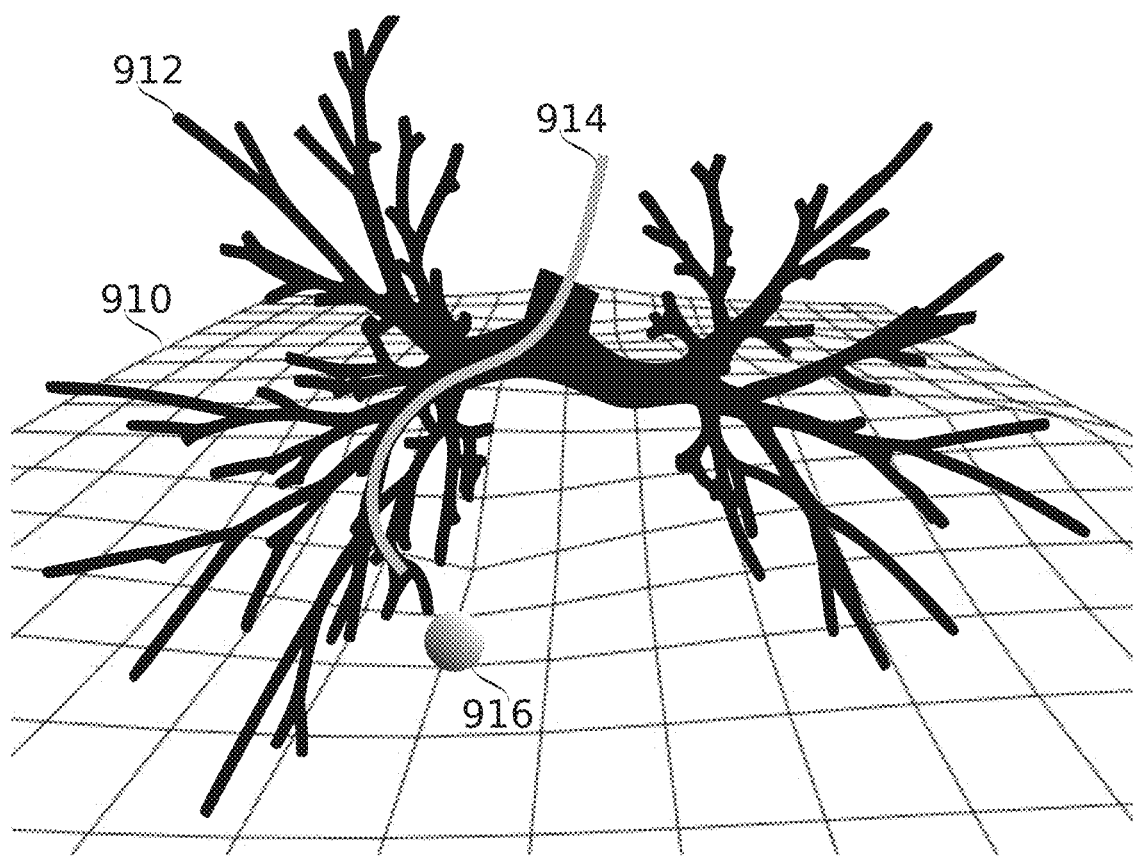
FIG. 9C schematically illustrates a CT section extending along a geometrical sectioning surface defined to curve so that it includes regions of the original CT image which correspond to positions along a catheter pathway, according to some embodiments of the present disclosure.

Reference is now made to FIG. 9C, which schematically illustrates a CT section 910 extending along a geometrical sectioning surface defined to curve so that it includes regions of the original 3-D image of anatomy which correspond to positions along a convoluted pathway 914 through an anatomical structure, according to some embodiments of the present disclosure. In some embodiments, pathway 914 is a pathway through airways. In some embodiments, pathway 914 is defined by the shape and position of an interventional instrument. In some embodiments, pathway 914 is defined to use as waypoints anatomical features such as a treatment target, blood vessels, or other structures of interest. Pathway 914 may be defined based on conditions during a procedure (e.g., a current position of an interventional instrument), and/or include predefined section, e.g., a planned pathway to reach a target of the interventional instrument.

CT section 910 corresponds to data of a source CT image located at positions intersected by a surface extending through the volume of the 3-D image, the surface itself including positions along pathway 914.

In some embodiments, pathway 914 is rendered to correspond to a 3-D shape corresponding to a measured shape of an interventional instrument to which it corresponds, and CT section 910 is distorted from its original coordinates to maintain region correspondence. In some embodiments, interventional instrument pathway 914 and CT section 910 are shown together in a composite 3-D scene which also includes a rendered mesh view of a deformation model 912.

With a single-sensor interventional instrument a deformed CT slice 910 may be displayed, for example using the low resolution deformation grid described above, reflecting the total deformation of the lungs and centered at the tip of the interventional instrument. The CT slice 910 may be global (reaching the CT boundaries) or local (surrounding a particular pathway through the airways of the lungs, e.g., as described in relation to FIGS. 10A-10B). With a fully tracked interventional instrument, the displayed CT slice may be geometrically curved such that it crosses all or most of the interventional instrument's curve (not just the tip), making it non-planar. Such a curved CT slice will display deformed anatomical features along the full interventional instrument length, which provides valuable information for NB procedures (for example, locations of blood vessels, fissures, diaphragm, and/or pleura). The curved CT slice may also cross specific important anatomical features. For example, the curved CT slice may cross the next-in-navigation bifurcation in the airways map, so that the bifurcation's cross-section is displayed in the slice in front of the interventional instrument. A potential advantage of using the curved CT slice is to compress the (deformed) 3-D CT volume into a 2-D view which encodes most of the valuable anatomical features for navigation at the area of the interventional instrument.

Since not all important anatomical features always lie on a smooth 2-D curved surface, the specific shape of the curved CT slice can be solved in an optimization process, searching for a 2-D curved surface which approximates in position and orientation a list of important features (e.g., interventional instrument pathway 914 and/or target 916) with weights describing the importance of each feature. The optimization process may include weights to penalize excessive distortion; for example, optimization may penalize deep and/or sharp bending angles, and/or penalize extreme curvatures based on the amount of added surface area which they contribute. The final result is a curved CT slice which compresses the deformed 3-D volume into a compact 2-D CT view.

While a CT image is described in FIG. 9C as an example, it should be understood that the display method is optionally performed using another 3-D image type, for example an MRI image, ultrasound image, and/or positron emission tomography (PET) scan image. Optionally, slices from two or more 3-D images (optionally of different imaging modality types) are combined.

Figure 10A:
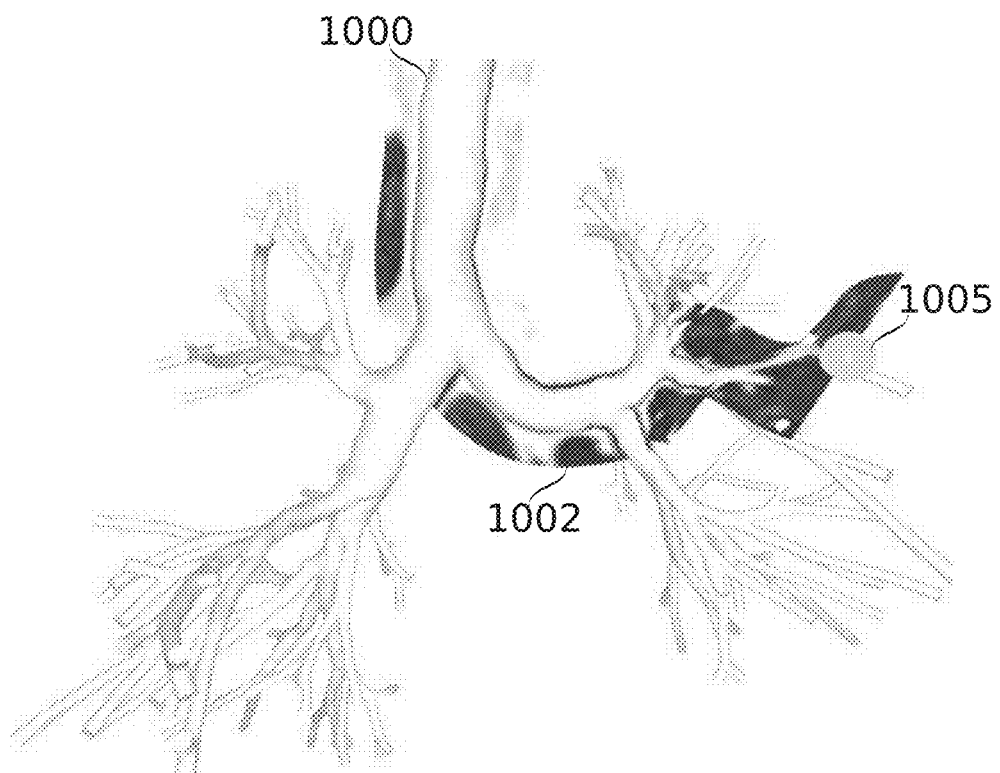
FIGS. 10A-10B schematically illustrate a CT strip along a pathway in a composite-D scene including a rendered mesh view of a deformation model before (FIG. 10A) and after (FIG. 9B) deformation, according to some embodiments of the present disclosure.
Figure 10B:
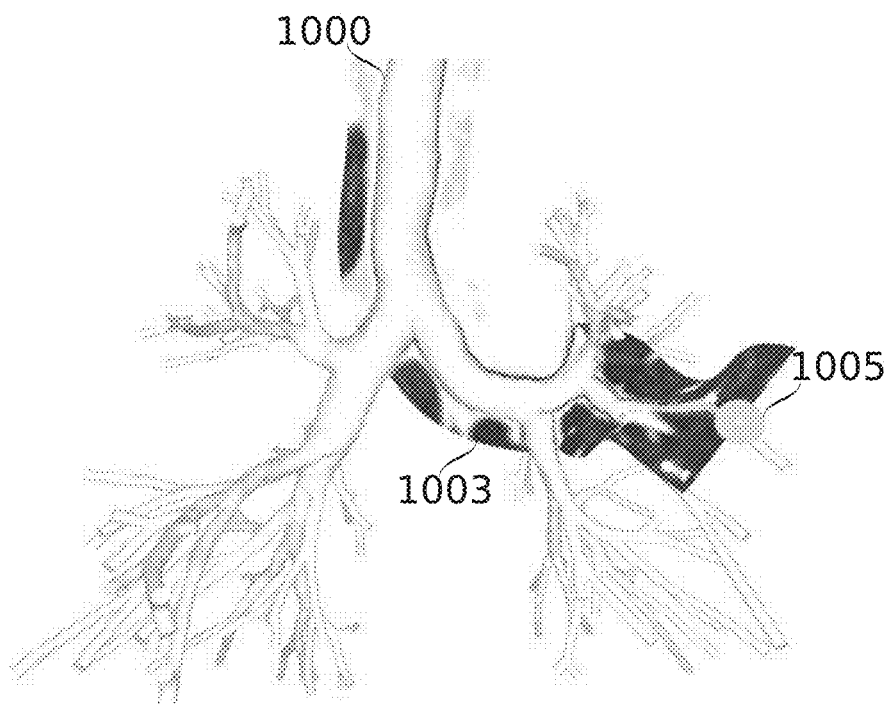

Reference is now made to FIGS. 10A-10B, which schematically illustrate a CT strip 1002, 1003 along a pathway in a composite 3-D scene including a rendered mesh view of a deformation model before (FIG. 10A) and after (FIG. 10B) deformation, according to some embodiments of the present disclosure.

The low resolution 2-D deformation grid described in relation to FIGS. 9A-9B allows rapid computation of the deformation of any pixel in between grid points by means of interpolation, which enables real-time display of deformed CT slices. The same technique can be generalized in order to create a 3-D deformation grid which covers the entire CT (or other 3-D image) volume. Deformation is computed for each control point of the grid and can be then interpolated to voxels in between grid points. The 3-D deformation grid enables fast computation for deformation anywhere inside the imaged volume. This may enable a real-time display of deformed-lung 3-D views such as deformed virtual bronchoscopy or deformed virtual fluoroscopy, both using raycasting rendering techniques. In a standard virtual bronchoscopy view, a virtual camera is positioned inside the airways. Each pixel on the screen represents a single virtual ray of light which steps through the imaged voxels to accumulate a final shading for that pixel. The final result is a realistic image which looks similar to that of a true bronchoscope inside the airways. While a standard virtual bronchoscopy algorithm samples a static CT volume in its ray tracing steps, the 3-D deformation grid may be used in a dynamic virtual bronchoscopy algorithm to create a ray traced image of the deformed CT volume. Instead of sampling the voxels of the static 3-D image, on each ray tracing step each ray's location is transformed using the 3-D deformation grid into its deformed location inside the initial, non-deformed 3-D image, which effectively results in sampling the real-time deformed CT.

During an NB procedure, a physician guides a tool (e.g., an interventional instrument) to follow a pathway from the trachea 1000 to the target 1005. The pathway can be displayed as a 3-D centerline inside the airways map. The physician may be presented with raw CT data around the interventional instrument using a local CT slice centered at the interventional instrument or the interventional instrument's tip, as described above, or the system may render a full CT strip (optionally a strip extending to about an equal distance on either side of the pathway) in 3-D along the pathway, for example, as shown in FIGS. 10A-10B. When the lungs deform (e.g., as indicated by measurements of the position of the interventional instrument and/or another parameter, the CT data displays to its deformed location, along with other anatomical deformed features. In order to deform a CT slice, its position in space can be deformed to the deformed location (while preserving its original CT data), or its position in space can remain fixed while deforming its CT data. Since the 3-D CT strip is naturally bound to airways, it is deformed in space together with the airways, as shown in FIGS. 10A-10B. Thus, the 3-D CT strip keeps its original CT data but its position in space is smoothly deformed together with the airways, similarly to deforming the 3-D airways map.

Figure 11:
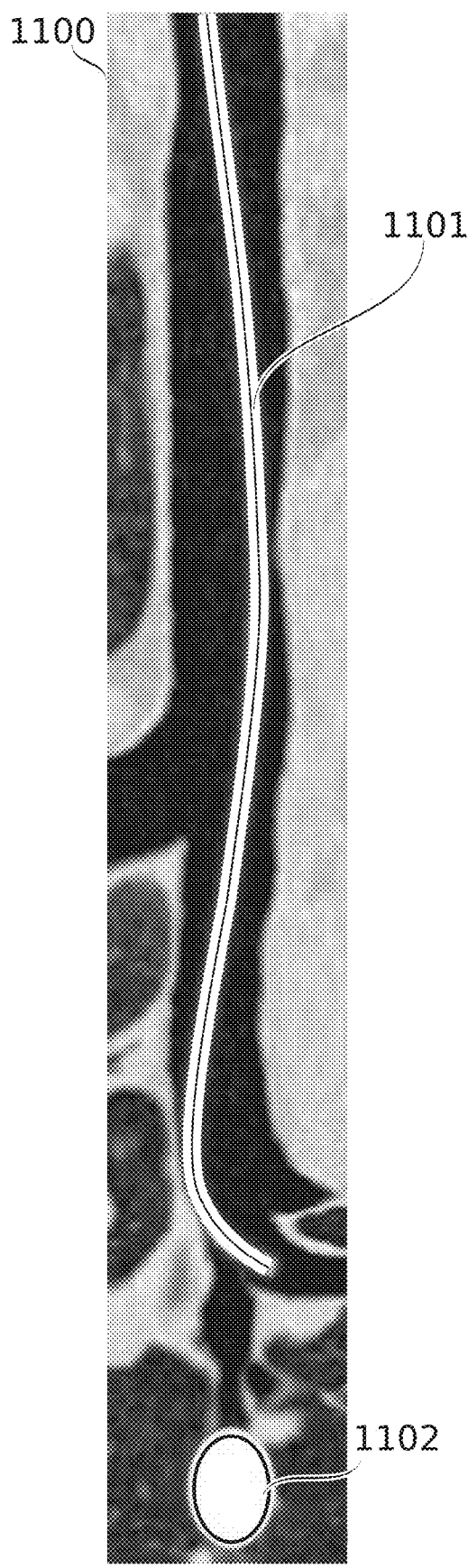
FIG. 11 illustrates a flattened strip of CT image data, extracted from along a-D path followed by a catheter, according to some embodiments of the present disclosure.

Reference is now made to FIG. 11, which illustrates a flattened strip 1100 of CT image data, extracted from along a 3-D path followed by an interventional instrument 1101, according to some embodiments of the present disclosure.

The same 3-D CT strip shown in FIGS. 10A-10B is optionally used to produce a 2-D path view in which the CT strip 1100 is displayed as a static 2-D background image, with the interventional instrument 1101 and/or target 1102 is projected on top of the static image in pathway coordinates. Similarly to the 3-D CT strip, this view potentially encodes most important anatomical information for navigating along a pathway to a specific target, but it is projected in a 2-D view which shows the entire pathway as a flat surface from beginning to end, independently of 3-D camera location and free from 3-D occlusions which may happen in the 3-D CT strip view as can be seen in FIGS. 10A-10B. A potential advantage of the 2-D path view is its locality, making it invariant to deformation. When deformation is applied, the CT strip follows the deformed airways (as discussed above) and so it doesn't change, and the interventional instrument usually keeps its position inside the pathway (e.g., in pathway coordinates).

Applying the deformation model to all displayed 2-D/3-D objects, including the 3-D airways mesh as well as CT slices allows producing a composite deformed scene in real-time. For example, during the patient's breathing, the breathing 3-D airways map may be displayed, overlaid by the breathing CT slice, in perfect sync with the patient's breathing. As another example: during steering, the interventional instrument may apply forces on the airways inside of which it navigates. The system can then display how the 3-D airways deform in real-time in reaction to the interventional instrument's steering (based on the deformation model) as well as displaying the corresponding deformed version of a local CT slice, at the proximity of the navigated airways. The physician is then displayed with real-time deformed anatomical data containing both the navigated airways, as well as anatomical deformed raw features from the CT volume, which are valuable for guidance, biopsy and treatment.

Figure 12:
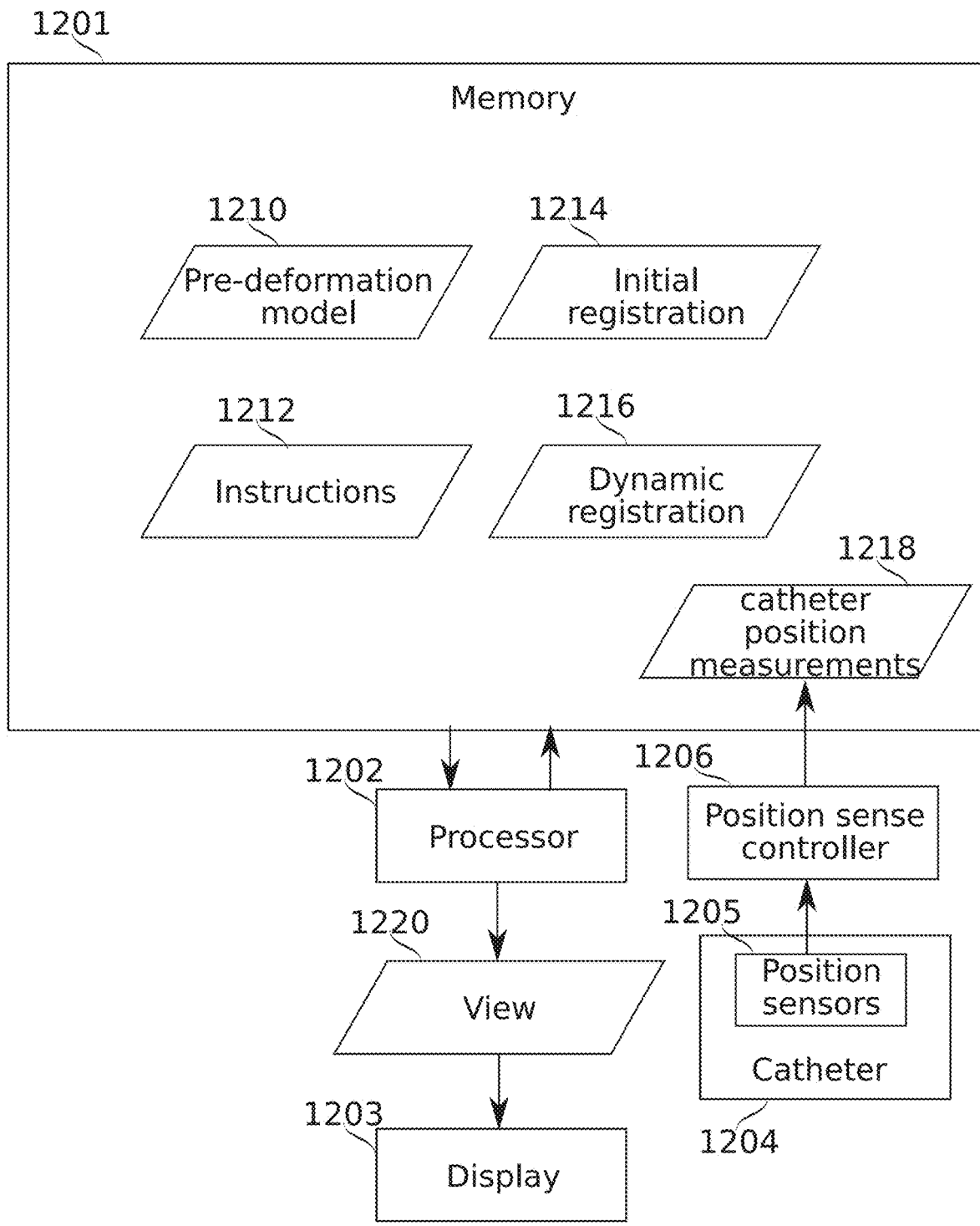
FIG. 12 schematically illustrates a system for tracking movement of a catheter within airways of a lung, according to some embodiments of the present disclosure.

Reference is now made to FIG. 12, which schematically illustrates a system for tracking movement of an interventional instrument within airways of a lung, according to some embodiments of the present disclosure.

Hardware components of the system of FIG. 12 include memory 1201, processor 1202, and optionally display 1203. Optionally, interventional instrument 1204 equipped with one or more position sensors 1205 is provided with the system, optionally along with position sense controller 1206. Position sensors 1205 may be located, e.g., at the tip of interventional instrument 1204, and/or at positions along the body of interventional instrument 1204.

Optionally all or part of the subsystem comprising interventional instrument 1204 and position sensing controller 1206 is provided separately.

Selected data structures used and/or generated in the operation of the system of FIG. 12 are shown as blocks within memory 1201.

These include:
Instructions 1212, which instruct processor 1202 to perform operations of any one or more of the methods described herein, for example with respect to FIGS. 1, 5, 7A-7B, and 8A. Processor 1202 may produce and/or access any of the other data structures in accordance with instructions 1212.

Pre-deformation model 1210, corresponding, for example, to the model produced at block 110 of FIG. 1, and/or the baseline airways map 503 of FIG. 5.

Initial registration 1214, which corresponds, for example, to the registration applied by block 504 of FIG. 5 and/or transformation state vector 710 of FIG. 7A.

Interventional instrument position measurements 1218, which correspond, for example, to position data 505 of FIG. 5.

Dynamic registration 1216, which corresponds, for example, to the dynamic transformation state vector 712 of FIG. 7A.

Instructions 1212 may instruct processor 1202 to produce one or more views 1220 representing a modified (e.g., initially and/or dynamically registered) version of pre-deformation model 1210, and provide them to display 1203. Block 1220 illustrates views provided as data streamed to display 1203. Data structures representing these views and/or intermediate data structures used in generating these views may also be produced by processor 1202 and stored in memory 1201 (not shown explicitly). Views 1220 may be produced, for example, as described in relation to FIGS. 8A-11.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of modeling a deformed state of a branched anatomical structure within which an interventional instrument is navigated, the method comprising:

accessing a baseline model constructed using imaged shapes of branches and bifurcations of the branched anatomical structure;

accessing a plurality of measurements of interventional instrument shape and position made using the interventional instrument while inserted within the branched anatomical structure, including at least two measurements of shape and position made while the interventional instrument is within, respectively, at least two of the branches which connect on a proximal side to a same bifurcation;

calculating a deformation defining modifications of the baseline model based on the plurality of measurements, the modifications including modifications to modeled branches representing the at least two of the branches; and producing a deformed model by modifying the baseline model according to the deformation, thereby registering the interventional instrument to the deformed state of the branched anatomical structure.

2. The method of claim 1, wherein the calculating uses an error function defining error of the modifications with respect both a target goal and shape constraints.

3. The method of claim 2, wherein the target goal characterizes deviation of the deformed model from a shape of the branched anatomical structure defined by the plurality of measurements in terms of error increasing as a function of deviation from the shape of the branched anatomical structure.

4. The method of claim 2, wherein the shape constraints characterize anatomical constraints on the modifications in terms of error increasing as a function of deviation from the baseline model weighted by a deformation model.

5. The method of claim 1, wherein each measurement of interventional instrument shape and position describes a shape and position of a curve of the interventional instrument.

6. The method of claim 2, comprising:
calculating and producing a dynamically deformed model modifying the deformed model based on a further measurement of interventional instrument shape and position;
wherein the calculating uses a second error function defining shape constraints in terms of error increasing as a function of deviation from the deformed model.

7. The method of claim 1, wherein each of the plurality of measurements of shape and position associates with a respective breathing phase.

8. The method of claim 7, comprising determining deformation parameters of the modeled branches in each of a plurality of modeled breathing phases using measurements of shape and position associated with the modeled breathing phase.

9. The method of claim 1, wherein calculating the deformed model comprises selecting measurements of the plurality of measurements measured during a selected breathing phase, and using the selected measurements to calculate breathing phase-dependent modifications of the baseline model; and the producing comprises modifying the baseline model to represent a breathing phase-dependent shape of the deformed model.

10. The method of claim 1, wherein producing the deformed model comprises calculating a modeled shape of the branched anatomical structure for at least one breathing phase by combining modeled shapes for at least two other breathing phases.

11. The method of claim 10, wherein the calculating a modeled shape comprises interpolating between the at least two other breathing phases.

12. The method of claim 1, wherein each of the baseline model and deformed model comprises a skeletonized model, wherein the branches and bifurcations of the branched anatomical structure correspond to the modeled branches of each model, represented as segments joined at modeled bifurcations.

13. The method of claim 1, wherein each of the accessed plurality of measurements measures interventional instrument shape as a plurality of position measurements at positions along the interventional instrument, each said position measurement being encoded in a system of probe localization coordinates comprising at least three position axes measured by a sensor at said respective position.

14. The method of claim 13, wherein the deformed model registers the system of probe localization coordinates to the imaged shapes of the branches and the bifurcations via the modifications of the baseline model.

15. The method of claim 13, wherein the probe localization coordinates comprise at least one orientation coordinate measured by a sensor at said respective position.

16. The method of claim 1, wherein producing the deformed model comprises:
encoding modifications of the modeled branches in an error function;
wherein the error function:
encodes localization errors in the deformed model relative to the accessed plurality of measurements; and
includes anatomical constraints which limit how the baseline model can be modified to reduce the localization errors in the deformed model.

17. The method of claim 1, comprising:
receiving reference measurements from one or more reference sensors attached at fixed anatomical positions to a body comprising the branched anatomical structure;
wherein the calculating comprises using the reference measurements to roughly register the plurality of measurements of interventional instrument shape and position to the branched anatomical structure.

18. The method of claim 1, comprising receiving reference measurements from one or more reference sensors; and assigning a breathing phase to each measurement of interventional instrument shape and position, using the reference measurements.

19. The method of claim 1, wherein producing the deformed model comprises transforming to the baseline model using a rigid transformation determined using the measured shapes and positions, and then modifying the transformed model according to the deformation model.

20. The method of claim 1, wherein:
the plurality of measurements of interventional instrument shape and position include measurements made by at least one additional interventional instrument inserted into the branched anatomical structure concurrently with the interventional instrument; and
the interventional instrument is inserted to a branch of the branched anatomical structure not occupied by the at least one additional interventional instrument.

21. The method of claim 1, comprising:
accessing at least one further measurement of interventional instrument shape and position made using the interventional instrument while inserted within the branched anatomical structure; and
modifying the deformed model to reduce an error function including:
a target goal condition decreasing the error function with reduced localization errors in the modified deformed model relative to the accessed at least one further measurement, and
a shape constraints condition increasing the error function with increasing difference of the modified deformed model from the deformed model, weighted according to a deformation model.

22. The method of claim 21, comprising calculating reduction of the error function, including:
converging to a minimized error function value from each of a plurality of initial states to a respective convergence target; and
selecting from among the convergence targets to define the modifications of the deformed model, according to the minimized error function values.

23. The method of claim 21, wherein the plurality of initial states include initial deformation states distinguished by different deformations of the deformed model.

24. The method of claim 21, wherein the plurality of initial states are distinguished by different hypotheses about a path that the interventional instrument follows within the branched anatomical structure.

25. The method of claim 21, wherein the converging and selecting implement a global search for a minimum of the error function.

26. The method of claim 21, wherein producing the deformed model comprises propagating changes modifying relative orientations of branches in a parent bifurcation of the model, to changes modifying spatial offsets and orientations of branches of child bifurcations of the parent bifurcation, thus propagating deformations beyond positions that were directly measured.

27. The method of claim 21, wherein the deformation model models propagation of a local deformation through tissue.

28. The method of claim 21, wherein the deformed model comprises a skeletonized model representing the branches and bifurcations of the branched anatomical structure as segments connected at modeled bifurcations; and the deformation model models error according to movement and bending of the segments relative to the deformed model.

29. The method of claim 28, wherein the modeled error changes as segments at a common bifurcation to change their relative angles.

30. The method of claim 28, wherein the modeled error changes according to anchoring forces exerted from a distal side of at least some of the segments.

31. The method of claim 28, wherein the modeled error changes according to bending along the length of at least some of the segments.

32. The method of claim 28, wherein the modeled error changes according to separations of segments not directly connected through the branching structure.

33. The method of claim 28, wherein the modeled error limits segments forming a global shape which is inconsistent with a range of a global shapes represented by a data set comprising a plurality of global shapes.

34. The method of claim 28, wherein the modeled error limits segments forming a branch shape which is inconsistent with a range of a branch shapes represented by a data set comprising a plurality of branch shapes.

35. The method of claim 21, wherein:
the further measurements of interventional instrument shape and position include measurements made by at least one additional interventional instrument inserted into the branched anatomical structure concurrently with the interventional instrument; and the interventional instrument is inserted to a branch of the branched anatomical structure not occupied by the at least one additional interventional instrument.

36. A system modeling a deformed state of a branched anatomical structure within which an interventional instrument is navigated, the system comprising a memory storing instructions and processor, wherein the memory instructs the processor to:

access a baseline model constructed using imaged shapes of branches and bifurcations of the branched anatomical structure;

access a plurality of measurements of interventional instrument shape and position made using the interventional instrument while inserted within the branched anatomical structure, including at least two measurements of shape and position made while the interventional instrument is within, respectively, at least two of the branches which connect on a proximal side to a same bifurcation;

calculate a deformation defining modifications of the baseline model based on the plurality of measurements, the modifications including modifications to modeled branches representing the at least two of the branches; and produce a deformed model by modifying the baseline model according to the deformation, thereby registering the interventional instrument to the deformed state of the branched anatomical structure.

37. The system of claim 36, wherein:

the processor calculates the deformation using an error function defining error of the modifications with respect both a target goal and shape constraints;

the target goal characterizes deviation of the deformed model from a shape of the branched anatomical structure defined by the plurality of measurements in terms of error increasing as a function of deviation from the shape of the branched anatomical structure; and the shape constraints characterize anatomical constraints on the modifications in terms of error increasing as a function of deviation from the baseline model weighted by a deformation model.

38. The system of claim 37, wherein:

the processor calculates and produces a dynamically deformed model modifying the deformed model based on a further measurement of interventional instrument shape and position, using a second error function defining shape constraints in terms of error increasing as a function of deviation from the deformed model; and the processor reduces the second error function by:

converging to a minimized error function value from each of a plurality of initial states to a respective convergence target; and selecting from among the convergence targets to define the modifications of the deformed model, according to the minimized error function values.

39. The system of claim 36, wherein each of the plurality of measurements of shape and position associates with a respective breathing phase.

40. The system of claim 39, comprising determining deformation parameters of the modeled branches in each of a plurality of modeled breathing phases using measurements of shape and position associated with the modeled breathing phase.

41. The system of claim 36, wherein calculating the deformed model comprises selecting measurements of the plurality of measurements measured during a selected breathing phase, and using the selected measurements to calculate breathing phase-dependent modifications of the baseline model; and the producing comprises modifying the baseline model to represent a breathing phase-dependent shape of the deformed model.

42. The system of claim 36, wherein producing the deformed model comprises calculating a modeled shape of the branched anatomical structure for at least one breathing phase by combining modeled shapes for at least two other breathing phases.

43. The system of claim 42, wherein the calculating a modeled shape comprises interpolating between the at least two other breathing phases.

44. The system of claim 36, wherein:

the deformed model comprises a skeletonized model representing the branches and bifurcations of the branched anatomical structure as segments connected at modeled bifurcations;

the deformation model models error according to movement and bending of the segments relative to the deformed model; and the processor uses the modeled error to limit at least one of the group consisting of:

changes as segments at a common bifurcation to change their relative angles, changes according to anchoring forces exerted from a distal side of at least some of the segments, changes according to bending along the length of at least some of the segments, changes according to separations of segments not directly connected through the branching structure, segments forming a global shape which is inconsistent with a range of a global shapes represented by a data set comprising a plurality of global shapes, and segments forming a branch shape which is inconsistent with a range of a branch shapes represented by a data set comprising a plurality of branch shapes.

45. The system of claim 36, comprising the interventional instrument, configured to be inserted into the branched anatomical structure.

* * * * *